US007026347B2

(12) United States Patent
Frydman et al.

(10) Patent No.: US 7,026,347 B2
(45) Date of Patent: Apr. 11, 2006

(54) PORPHYRIN-POLYAMINE CONJUGATES FOR CANCER THERAPY

(75) Inventors: Benjamin Frydman, Madison, WI (US); Aldonia L. Valasinas, Madison, WI (US); Venodhar K. Reddy, Madison, WI (US); Hirak S. Basu, Madison, WI (US); Aparajita Sarkar, Madison, WI (US); Subhra Bhattacharya, Madison, WI (US); Yu Wang, Madison, WI (US); Laurence J. Marton, Palo Alto, CA (US); Andrei V. Blokhin, Fitchburg, WI (US)

(73) Assignee: CellGate, Inc., Redwood City, CA (US)

( * ) Notice: Subject to any disclaimer, the term of this patent is extended or adjusted under 35 U.S.C. 154(b) by 0 days.

(21) Appl. No.: 10/606,016

(22) Filed: Jun. 24, 2003

(65) Prior Publication Data

US 2004/0152687 A1 Aug. 5, 2004

Related U.S. Application Data

(60) Provisional application No. 60/392,171, filed on Jun. 26, 2002.

(51) Int. Cl.
 A61K 31/40 (2006.01)
 A61K 31/555 (2006.01)
 A61B 5/055 (2006.01)
 A61B 10/00 (2006.01)
 C07B 47/00 (2006.01)
(52) U.S. Cl. ............... 514/410; 514/185; 424/9.362; 424/9.61; 540/145; 534/15
(58) Field of Classification Search ........... 540/145; 534/15; 514/185, 410; 424/9.1
 See application file for complete search history.

(56) References Cited

U.S. PATENT DOCUMENTS

| 4,443,604 | A | 4/1984 | Lee |
|---|---|---|---|
| 4,784,736 | A | 11/1988 | Lonsdale et al. |
| 5,275,801 | A | 1/1994 | Niedballa et al. |
| 5,912,341 | A | 6/1999 | Hoffman et al. |
| 6,114,321 | A | 9/2000 | Platzek et al. |
| 6,207,660 | B1 | 3/2001 | Sessler et al. |
| 6,395,257 | B1 | 5/2002 | Achilefu et al. |
| 6,906,050 | B1 | 6/2005 | Robinson |
| 2002/0155999 | A1 | 10/2002 | Han |
| 2003/0036538 | A1 | 2/2003 | Rajagopalan et al. |
| 2003/0100752 | A1 | 5/2003 | Robinson |
| 2004/0192665 | A1 | 9/2004 | Frydman et al. |

FOREIGN PATENT DOCUMENTS

| WO | WO 00/66587 | 11/2000 |
|---|---|---|
| WO | WO 200066587 A2 * | 11/2000 |
| WO | WO-02/10142 A1 | 2/2002 |
| WO | WO-03/004091 A2 | 1/2003 |
| WO | WO-03/004091 A3 | 1/2003 |
| WO | WO-03/004466 A2 | 1/2003 |
| WO | WO-03/004466 A3 | 1/2003 |
| WO | WO-03/051348 A2 | 6/2003 |
| WO | WO-2004/002991 A1 | 1/2004 |
| WO | WO-2004/012774 A1 | 2/2004 |
| WO | WO-2004/041828 A1 | 5/2004 |

OTHER PUBLICATIONS

Ando, A. et al. (Aug. 1990). "Synthesis of Fluorine Analogues of Protoporphyrin Potentially Useful for Diagnosis and Therapy of Tumors," *Chemical and Pharmaceutical Bulletin* 38(8):2175-2178.

Brunner, H. et al. (1994). "Platinum(II) Complexes With Porphyrin Ligands—Additive Cytotoxic and Photodynamic Effect," *Angew. Chem. Int. Ed. Engl*, 33(21):2214-2215.

Kramer, D.L. et al. (Dec. 15, 1997). "Effects of Novel Spermine Analogues on Cell Cycle Progression and Apoptosis in MALME-3M Human Melanoma Cells," *Cancer Research* 57:5521-5527.

Sharma, A. et al. (Aug. 1997). "Antitumor Efficacy of $N^1$, $N^{11}$-Diethylnorspermine on a Human Bladder Tumor Xenograft in Nude Athymic Mice," *Clinical Cancer Research* 3:1239-1244.

Stemberg, E. et al. (Aug. 1996), "Pyrrolic Photosensitizers," *Current Medicinal Chemistry* 3(4):239-272.

Wamser, C.C. et al. (1989), "Thin-Film Composite Membranes for Artificial Photosynthesis. Final Report, July 15, 1985-Mar. 31, 1989," *National Technical Information Service*, 41 pages.

* cited by examiner

*Primary Examiner*—James O. Wilson
*Assistant Examiner*—Matthew L. Fedowitz
(74) *Attorney, Agent, or Firm*—Morrison & Foerster LLP

(57) ABSTRACT

Porphyrin-polyamine conjugate compounds are disclosed which have anticancer and antitumor effects. The porphyrin moiety selectively localizes in tumors, while the polyamine moiety serves as a cytotoxic agent. Methods of making and using the porphyrin-polyamine conjugate compounds are also disclosed.

16 Claims, 14 Drawing Sheets

Figure 1:
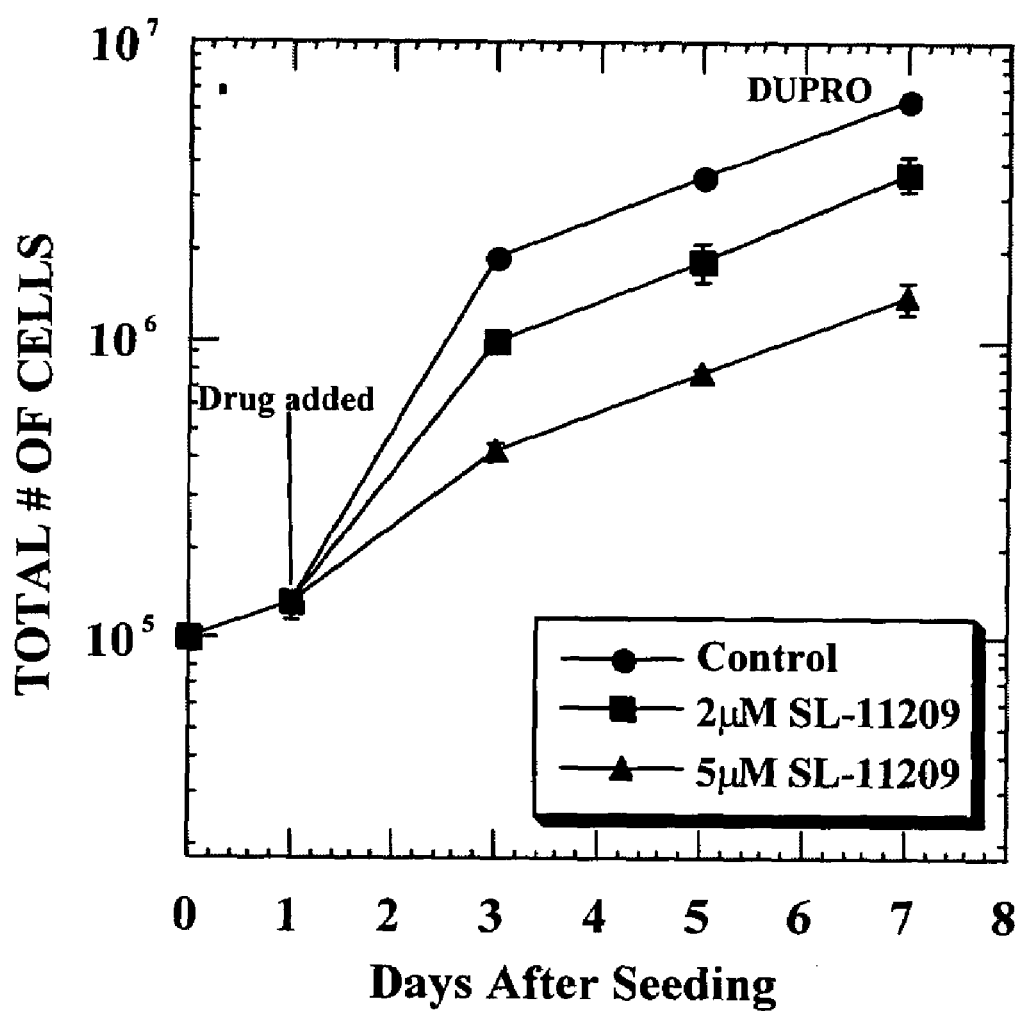

Oral 11237    Figure 14
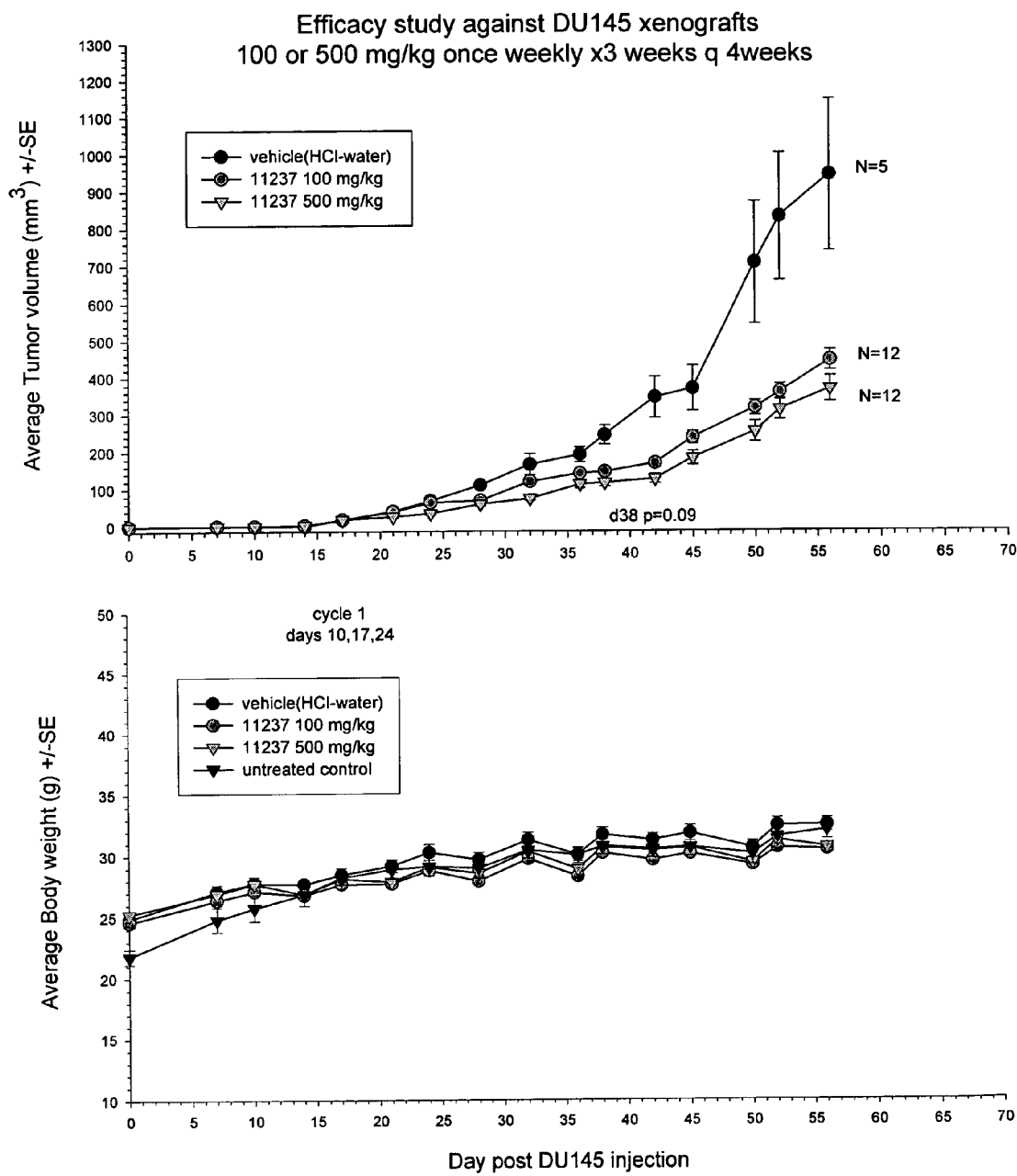
male athymic nude mice were given s.c. injections of 0.75 x10⁶ DU145 cells on Day 0.
beginning on Day 10 mice were treated once weekly for 3 weeks with acidified water,
100mg/kg or 500mg/kg SL-237 via oral gavage at 10 ml/kg dosing volume.
* The 3rd treatment was actually 400mg/kg in the high dose group.

PORPHYRIN-POLYAMINE CONJUGATES FOR CANCER THERAPY

CROSS-REFERENCE TO RELATED APPLICATIONS

This application claims priority benefit of U.S. Provisional Patent Application No. 60/392,171, filed Jun. 26, 2002. The content of that application is hereby incorporated by reference herein in its entirety.

STATEMENT REGARDING FEDERALLY SPONSORED RESEARCH OR DEVELOPMENT

Not applicable.

REFERENCE TO AN APPENDIX

Not applicable.

TECHNICAL FIELD

This invention relates to porphyrin-polyamine conjugate compounds used for treatment of cancer and other diseases.

BACKGROUND OF THE INVENTION

Cancer is the third most common cause of death in the world according to the World Health Organization, after heart disease and infectious disease. Cancer is the second most common cause of death (after heart disease) in the developed world. Accordingly, discovery of new and effective treatments for cancer is a high priority for health care researchers.

Cancer is often treated by using chemotherapy to selectively kill or hinder the growth of cancer cells, while having a less deleterious effect on normal cells. Chemotherapeutic agents often kill rapidly dividing cells, such as cancer cells; non-malignant cells which are dividing less rapidly are affected to a lesser degree. Other agents, such as antibodies attached to toxic agents, have been evaluated for use against cancers. These agents target the cancer cells by making use of a characteristic specific to the cancer, for example, higher-than-normal rates of cell division, or unique antigens expressed on the cancer cell surface.

As toxic agents specifically targeted against cancer cells can enhance therapeutic efficacy, reduce undesirable side effects, or both, many efforts have been made to achieve selective localization of well-defined chemical materials in malignant tumors. A significant advance in the field occurred with the introduction of tetraphenylporphine sulfonates (TPPS), which are non-naturally occurring porphyrins (Winkelman J. (1962) Cancer Res. 22:589). A hematoporphyrin derivative (HPD) was also found to localize in tumors (Lipson R L, Baldes, E J, & Gray M S (1967) Cancer 20: 2255). HPD is a complex mixture of porphyrins currently used as a sensitizer derivative that concentrates in tumor cells and destroys them after the tumor is irradiated with light or a laser beam (Dougherty T J, (1987) Photochem. Photobiol. 45:879). A wide variety of porphyrins and porphyrin analogues have been found to be selectively taken up by tumors, such as the naturally occurring porphyrins; for example, the octacarboxylic uroporphyrins, the tetracarboxylic coproporphyrins, and the dicarboxylic protoporphyrin. Synthetic porphyrins are also selectively taken up by tumors; among them are the meso-tetraphenyl porphyrins and the different porphyrin sulfonates $TPPS_4$, $TPPS_3$, $TPPS_{2a}$ and $TPPS_1$, which are listed in order of decreasing number of sulfonic acid substituents and decreasing hydrophilicity. Many factors determine the uptake and concentration of porphyrins in the tumors; one important factor is the structure (hydrophobicity, size, polarity) of the drug; another important factor is the formulation in which it is delivered (Sternberg E and Dolphin D (1996) Current Med Chemistry 3, 239). The mechanism(s) of porphyrin localization in tumors is still not entirely clear; the more hydrophobic porphyrins are preferentially incorporated in the lipid core of lipoproteins. Tightly aggregated porphyrins circulate as unbound pseudomicellar structures which can be entrapped in the interstitial regions of the tumor, can be localized in macrophages, or can enter neoplastic cells via pinocytotic processes. Low density lipoproteins (LDL), which are endocytosed by neoplastic cells through a specific receptor-mediated pathway, display the most selective release of porphyrins into the tumors (Jori G (1989) Photosensitizing Compounds, Ciba Foundation Symp 146, pp 78–94).

The present invention describes the synthesis and cytotoxic actions of porphyrin-polyamine conjugates. They are taken up by the tumor cells due to their porphyrin moiety, while the polyamine moiety provides the cytotoxic effects (see International Patent Application Nos. WO 00/66587 and WO 02/10142, and U.S. Pat. Nos. 6,392,098, 5,889,061, and 5,677,350).

SUMMARY OF THE INVENTION

The invention provides porphyrin-polyamine conjugate compounds and compositions comprising such compounds.

In one embodiment, the invention embraces a composition comprising a compound according to the formula

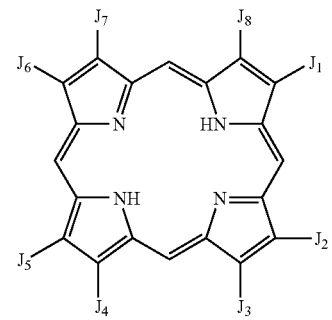

wherein at least one of $J_1$, $J_2$, $J_3$, $J_4$, $J_5$, $J_6$, $J_7$ and $J_8$ is independently M, where M is selected from the group consisting of

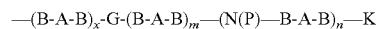

wherein each A is independently selected from the group consisting of: a nonentity, $C_1$–$C_{12}$ alkyl, $C_2$–$C_{12}$ alkenyl, $C_2$–$C_{12}$ alkynyl, $C_3$–$C_{12}$ cycloalkyl, $C_3$–$C_8$ cycloaryl, $C_3$–$C_{12}$ cycloalkenyl, $C_3$–$C_{12}$ cycloalkynyl, $C_1$–$C_{12}$ alkanol, $C_3$–$C_{12}$ cycloalkanol, and $C_3$–$C_8$ hydroxyaryl;

each B is independently selected from the group consisting of: a nonentity, $C_1$–$C_{12}$ alkyl, $C_2$–$C_{12}$ alkenyl, $C_2$–$C_{12}$ alkynyl, $C_3$–$C_{12}$ cycloalkyl, $C_3$–$C_8$ cycloaryl, $C_3$–$C_{12}$ cycloalkenyl, $C_3$–$C_{12}$ cycloalkynyl, $C_1$–$C_{12}$ alkanol, $C_3$–$C_{12}$ cycloalkanol, and $C_3$–$C_8$ hydroxyaryl;

and with the proviso that each —B-A-B— unit contain at least one carbon atom;

wherein G is independently selected from the group consisting of —N(P)—, —(C=O)—N(P)—, —N(P)—(C=O)—, and a nonentity;

x is independently 0 or 1;

m is independently 0 or 1;

n is independently an integer from 0 to 20;

each P is independently selected from the group consisting of H and $C_1$–$C_{12}$ alkyl;

K is independently selected from the group consisting of H, $C_1$–$C_{12}$ alkyl, $C_2$–$C_{12}$ alkenyl, $C_2$–$C_{12}$ alkynyl, $C_3$–$C_{12}$ cycloalkyl, $C_3$–$C_8$ cycloaryl, $C_3$–$C_{12}$ cycloalkenyl, $C_3$–$C_{12}$ cycloalkynyl, $C_1$–$C_{12}$ alkanol, $C_3$–$C_{12}$ cycloalkanol, and $C_3$–$C_8$ hydroxyaryl, and Q;

where each Q is independently selected from the group consisting of

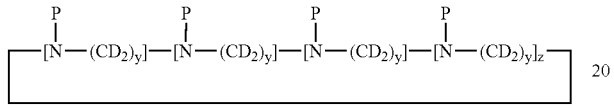

where each P is independently selected from the group consisting of H and $C_1$–$C_{12}$ alkyl, each D is selected from the group consisting of H and $C_1$–$C_{32}$ alkyl, y is an integer from 1 to 8, and z is an integer from 0 to 5, and where the Q moiety is attached to the remainder of the molecule at any C or N atom in the Q moiety (including C atoms in the D or P moieties) by removing a hydrogen atom, a P substituent, or a D substituent of the Q moiety to form an open valence for attachment to the remainder of the molecule;

and where the remaining members or member of $J_1$, $J_2$, $J_3$, $J_4$, $J_5$, $J_6$, $J_7$ and $J_8$ are each independently selected from the group consisting of H, —B-A-B, —COOH, —SO$_3$H, —B-A-B—COOH, or —B-A-B—SO$_3$H, where each A and each B are independently selected as defined above and with the proviso that each —B-A-B— unit has at least one carbon atom.

In another embodiment, M excludes moieties of the form

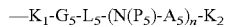

where $K_1$ is independently selected from the group consisting of $C_1$–$C_8$ alkyl and where the valence to the left of $K_1$ attaches to the porphyrin ring;

$G_5$ is —O—, —(C=O)—, —C(=O)—O—, —O—(C=O)—, —O—(C=O)—O—, —O—(C=O)—N—, —N—(C=O)—O—, or a nonentity;

$L_5$ is $C_1$–$C_8$ alkyl, $C_3$–$C_8$ cycloalkyl, $C_3$–$C_8$ cycloaryl, $C_1$–$C_8$ alkoxy, $C_1$–$C_8$ alkyl-$C_3$–$C_8$ cycloalkyl, $C_1$–$C_8$ alkyl-$C_3$–$C_8$ cycloaryl, $C_1$–$C_8$ alkoxy-$C_3$–$C_8$ cycloaryl, $C_3$–$C_8$ cycloalkyl-$C_3$–$C_8$ cycloaryl, $C_3$–$C_8$ cycloalkyl-$C_1$–$C_8$ alkyl, $C_3$–$C_8$ cycloaryl-$C_1$–$C_8$ alkyl, $C_3$–$C_8$ cycloaryl-$C_1$–$C_8$ alkoxy, $C_3$–$C_8$ cycloaryl-$C_3$–$C_8$ cycloalkyl, or a nonentity;

each $A_5$ is independently selected from the group consisting of $C_1$–$C_8$ alkyl, $C_2$–$C_8$ alkenyl, $C_2$–$C_8$ alkynyl, $C_3$–$C_8$ cycloalkyl, $C_3$–$C_8$ cycloaryl, $C_3$–$C_8$ cycloalkenyl, and $C_3$–$C_8$ cycloalkynyl;

$P_5$ is selected from the group consisting of H and $C_1$–$C_8$ alkyl;

n is an integer from 2 to 8;

and $K_2$ is independently selected from the group consisting of H, $C_1$–$C_8$ alkyl, $C_2$–$C_8$ alkenyl, $C_2$–$C_8$ alkynyl, $C_3$–$C_8$ cycloalkyl, $C_3$–$C_8$ cycloaryl, $C_3$–$C_8$ cycloalkenyl, $C_3$–$C_8$ cycloalkynyl, $C_1$–$C_8$ alkanol, $C_3$–$C_8$ cycloalkanol, and $C_3$–$C_8$ hydroxyaryl.

In another embodiment, G is independently selected from —(C=O)—N(P)— and —N(P)—(C=O)—. In another embodiment, the Q moiety is attached to the remainder of the molecule at any N atom in the Q moiety by removing a P substituent of the Q moiety to form an open valence for attachment to the remainder of the molecule. In another embodiment, each A and B substituent, if present, is selected from $C_1$–$C_{12}$ alkyl. In another embodiment, at least one A substituent comprises a cyclopropane group.

In another embodiment, the invention embraces a composition comprising a compound according to the formula

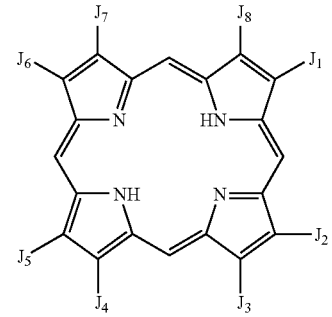

where $J_1$ and $J_2$ are independently —(B-A-B)$_x$-G-(B-A-B)$_m$—(N(P)—B-A-B)$_n$—K;

$J_3$, $J_4$, $J_6$ and $J_8$ are independently selected from methyl and ethyl; and $J_5$ and $J_7$ are independently selected from methyl, ethyl, and —SO$_3$H. In another embodiment, $J_1$ and $J_2$ are independently —(B-A-B)-G-(B-A-B)—(N(P)—B-A-B)$_n$—K. In another embodiment, at least one B-A-B unit comprises a cycloalkyl moiety, such as a cyclopropyl moiety. In another embodiment, $J_1$ and $J_2$ are independently —$C_1$–$C_{12}$ alkyl-G-$C_1$–$C_{12}$ alkyl-(N(P)—B-A-B)$_n$—K. In another embodiment, $J_1$ and $J_2$ are independently —$C_1$–$C_{12}$ alkyl-(C=O)—N(P)—$C_1$–$C_{12}$ alkyl-(N(P)—B-A-B)$_n$—K. In another embodiment, $J_1$ and $J_2$ are independently —(CH$_2$)$_2$C(=O)N(P$_2$)—$C_1$–$C_4$ alkyl-[NH(CH$_2$CH$_2$CH$_2$CH$_2$)]$_f$$C_1$–$C_{12}$ alkyl, where $P_2$ is H, methyl, or ethyl, and f is an integer from 1 to 10.

In still further embodiments, $J_1$ and $J_2$ are identical.

In still further embodiments, whenever any embodiment comprises a Q moiety (that is, whenever any K is Q), only one D moiety is selected from the group consisting of $C_1$–$C_{32}$ alkyl and all remaining D moieties are H; three P groups are selected from the group consisting of —H and —CH$_3$ and the fourth P group is absent and the Q moiety is attached to the remainder of the molecule at that valence; and y is 2,3, or 4 and z is 0, 1, or 2.

In further embodiments, whenever any embodiment comprises a Q moiety, Q can be

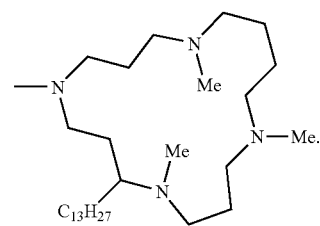

BRIEF DESCRIPTION OF THE DRAWING(S)

FIG. 1. is a graph depicting the in vitro effects of increasing concentrations of SL-11209 on the growth of cultured human prostate cancer cells DUPRO.

Figure 2:
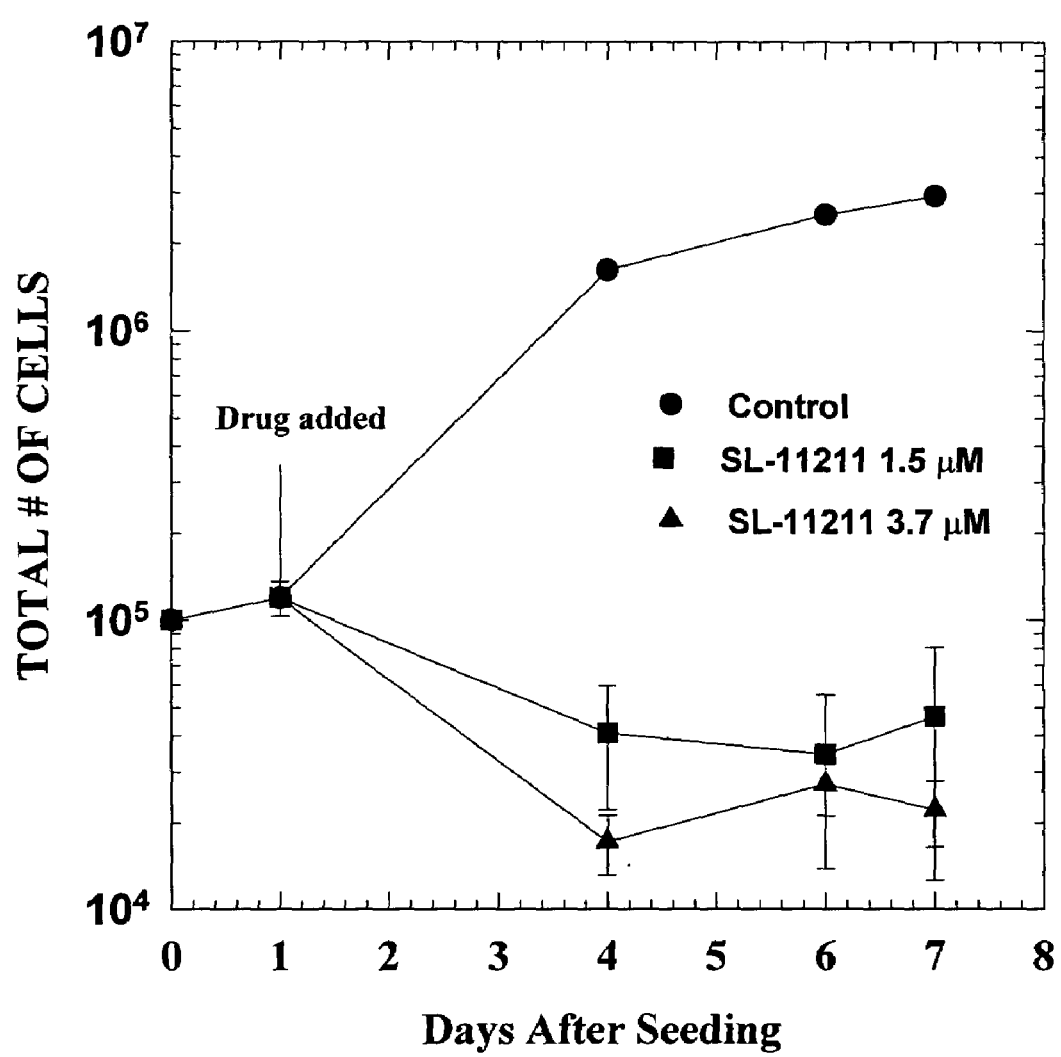

FIG. 2. is a graph depicting the in vitro effects of increasing concentrations of SL-11211 on the growth of cultured human prostate cancer cells DUPRO.

Figure 3:
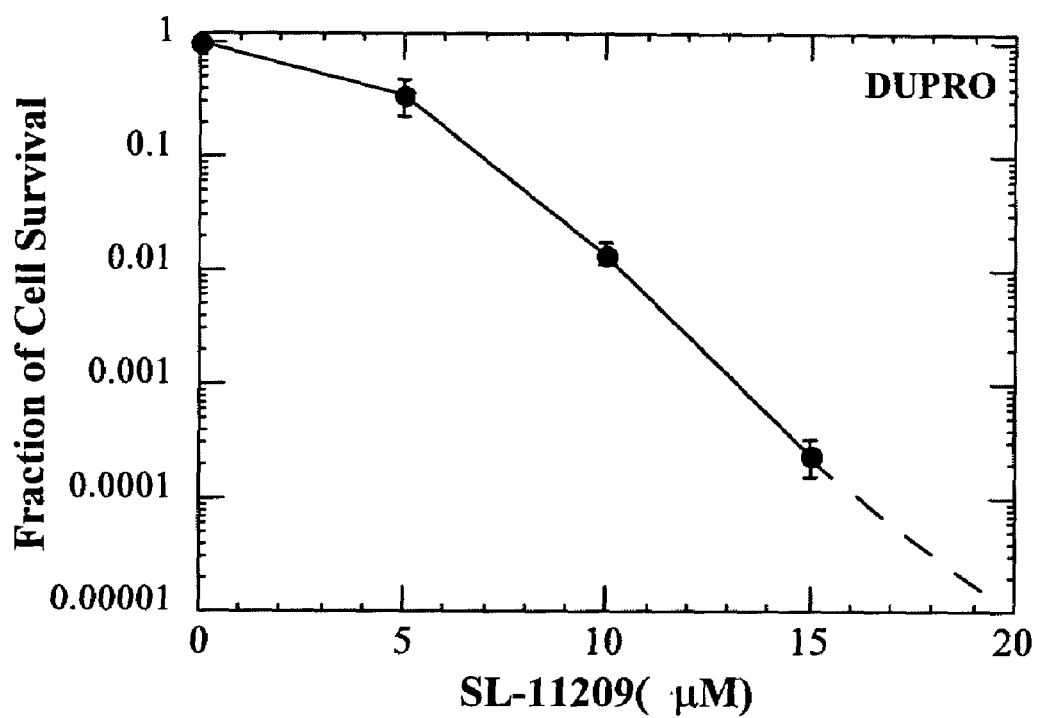

FIG. 3. is a graph depicting the in vitro effects of increasing concentrations of SL-11209 on the survival of cultured human prostate cancer cells DUPRO after 5 days of treatment.

Figure 4:
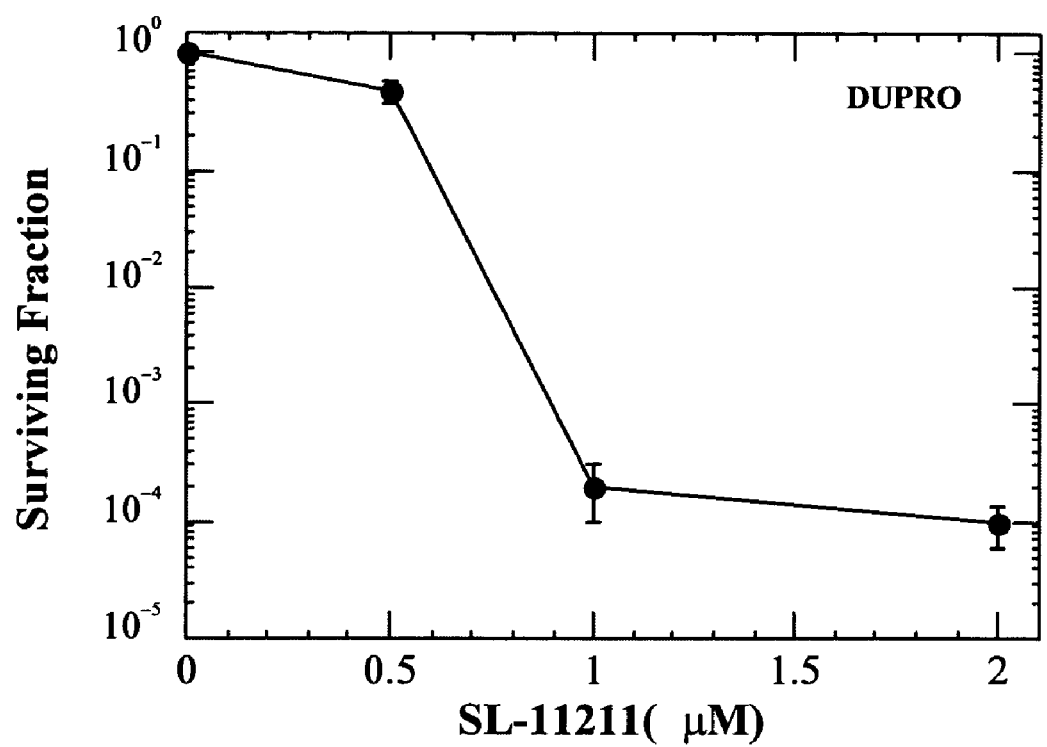

FIG. 4. is a graph depicting the in vitro effects of increasing concentrations of SL-11211 on the survival of cultured human prostate cancer cells DUPRO after 3 days of treatment.

Figure 5:
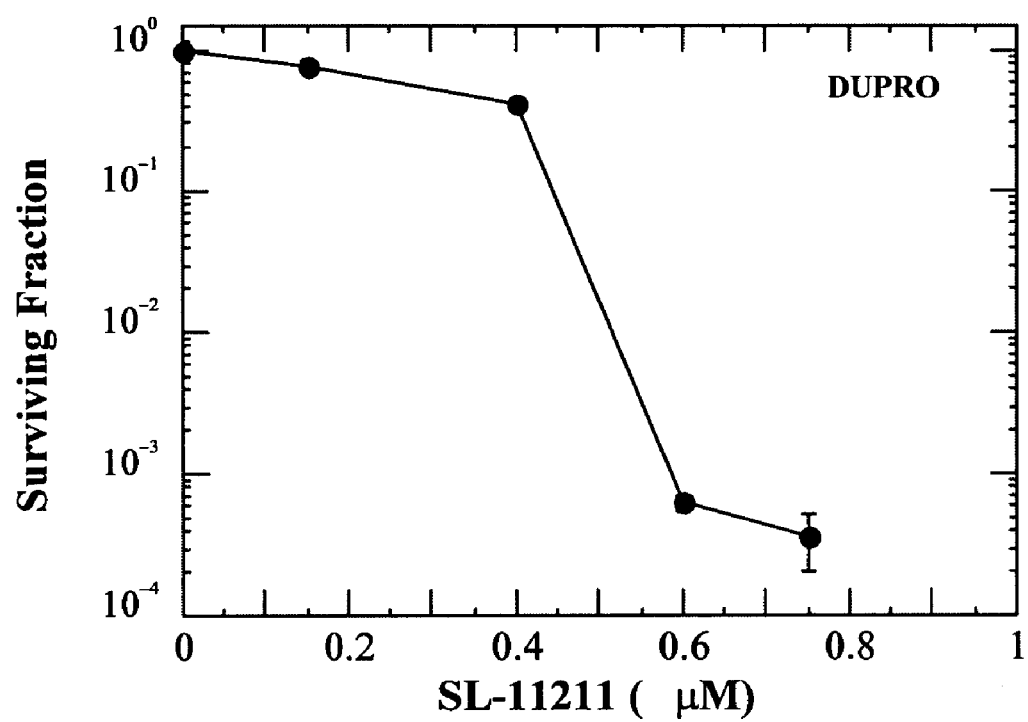

FIG. 5. is a graph depicting the in vitro effects of increasing concentrations of SL-11211 on the survival of cultured human prostate cancer cells DUPRO after 5 days of treatment.

Figure 6:
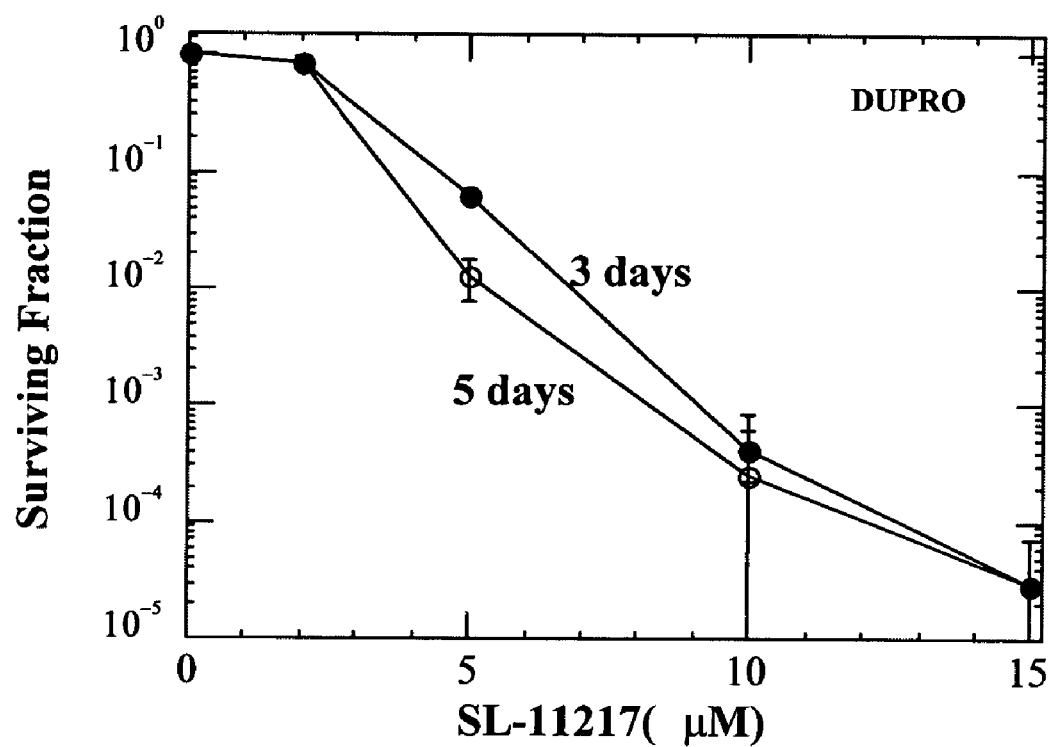

FIG. 6. is a graph depicting the in vitro effects of increasing concentrations of SL-11217 on the survival of cultured human prostate cancer cells DUPRO after 3 and 5 days of treatment.

Figure 7:
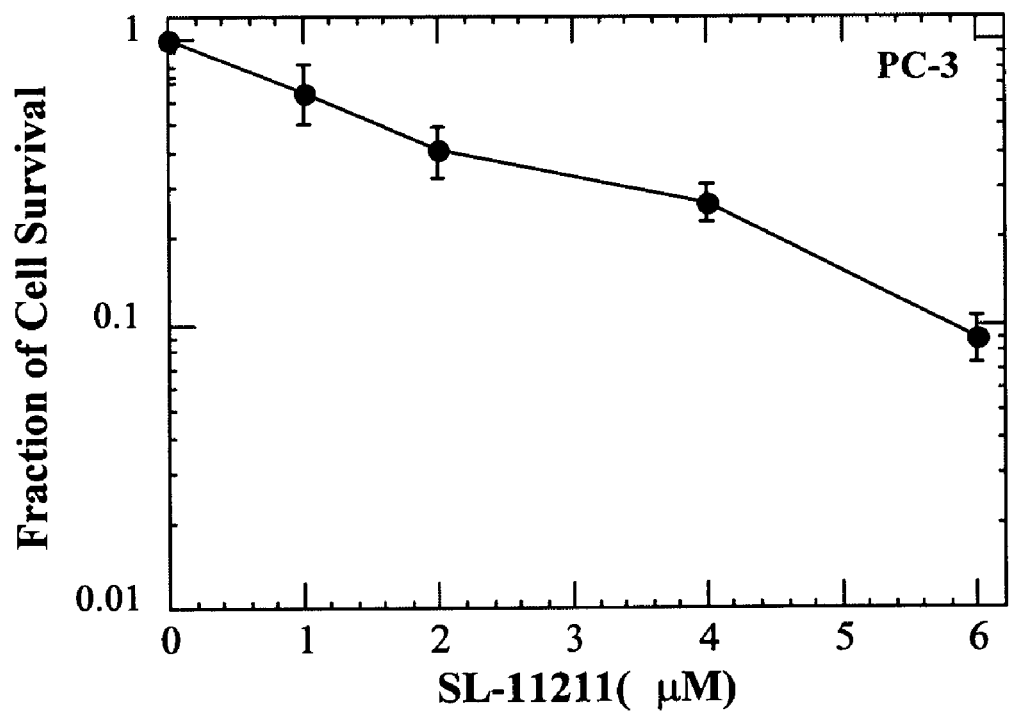

FIG. 7. is a graph depicting the in vitro effects of increasing concentrations of SL-11211 on the survival of cultured human prostate cancer cells PC3 after 5 days of treatment.

Figure 8:
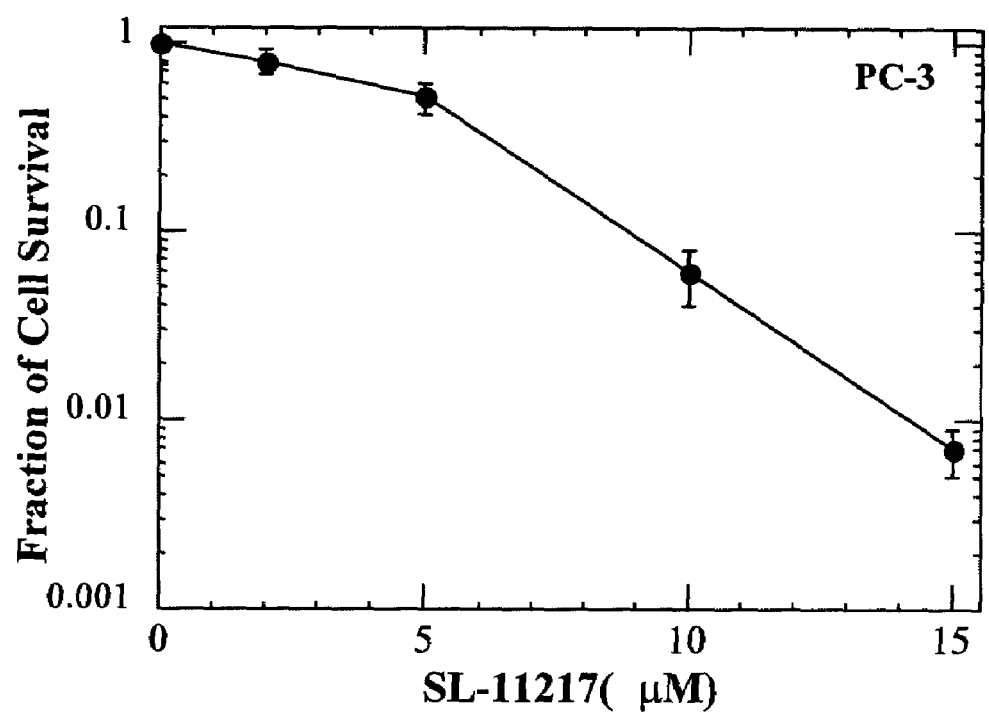

FIG. 8. is a graph depicting the in vitro effects of increasing concentrations of SL-11217 on the survival of cultured human prostate cancer cells PC3 after 5 days of treatment.

Figure 9:
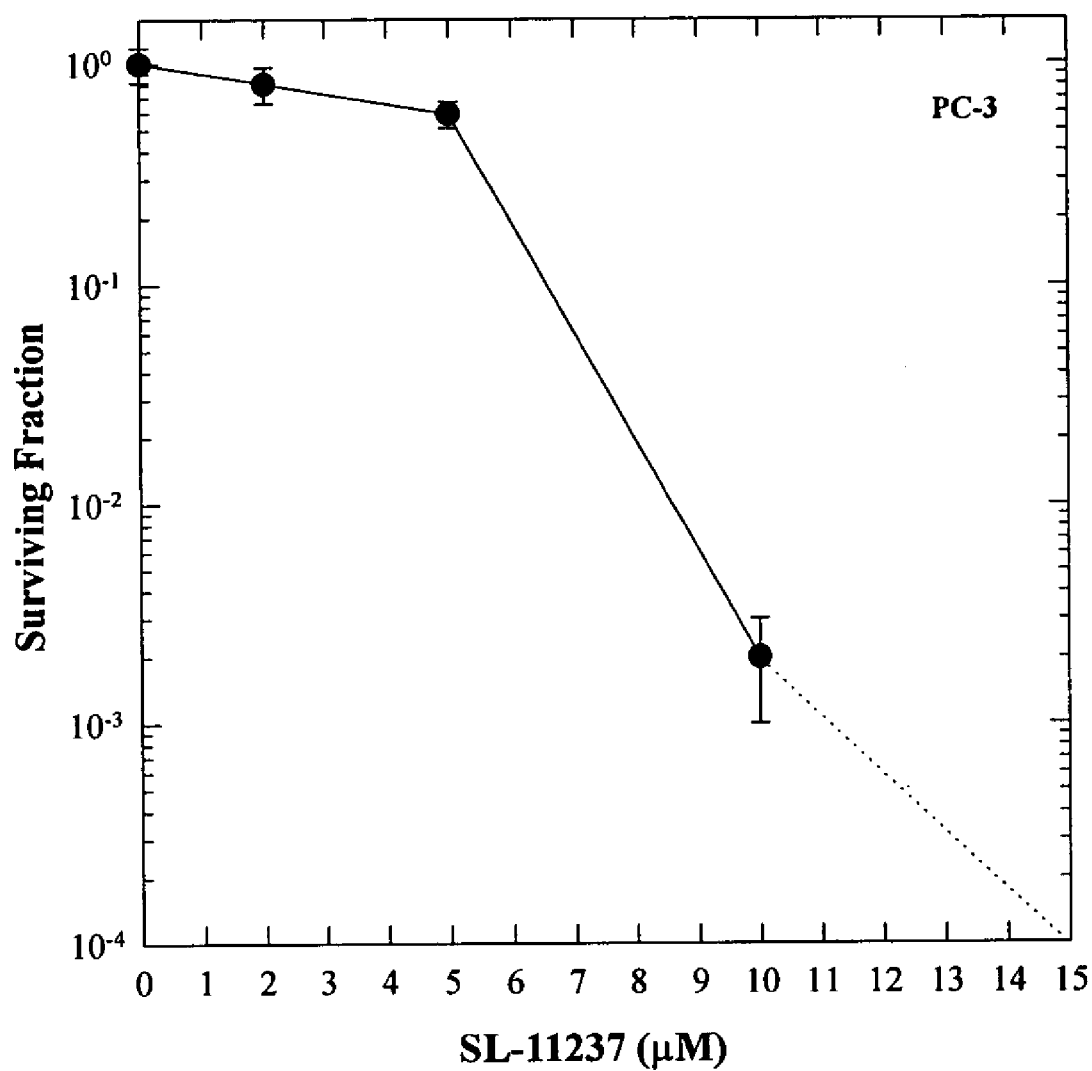

FIG. 9. is a graph depicting the in vitro effects of increasing concentrations of SL-11237 on the survival of cultured human prostate cancer cells PC3 after 5 days of treatment.

Figure 10:
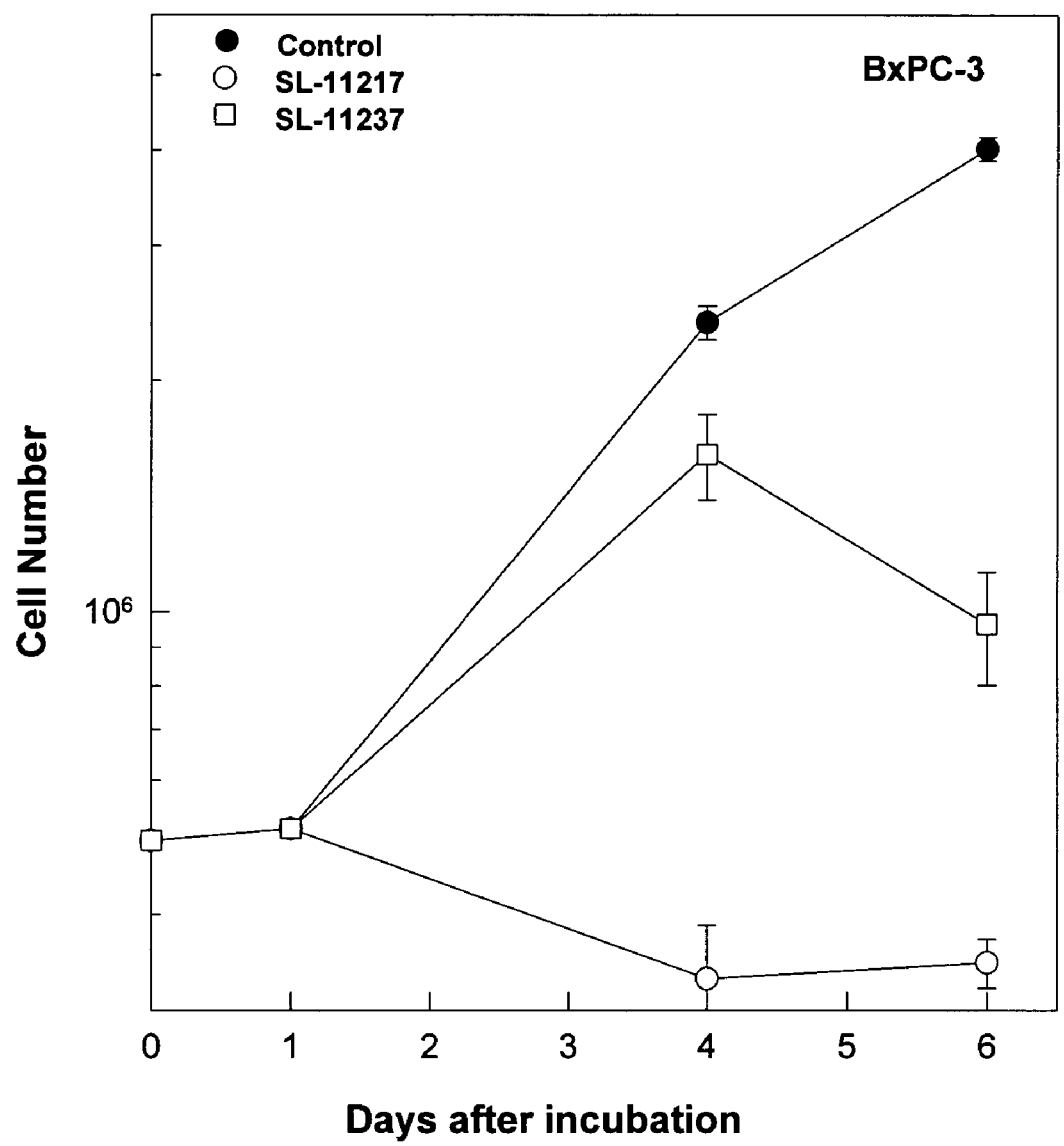

FIG. 10. is a graph depicting the in vitro effects of 10 µM SL-11217 and SL-11237 on the growth of cultured human pancreatic cancer cells BxPC3.

Figure 11:
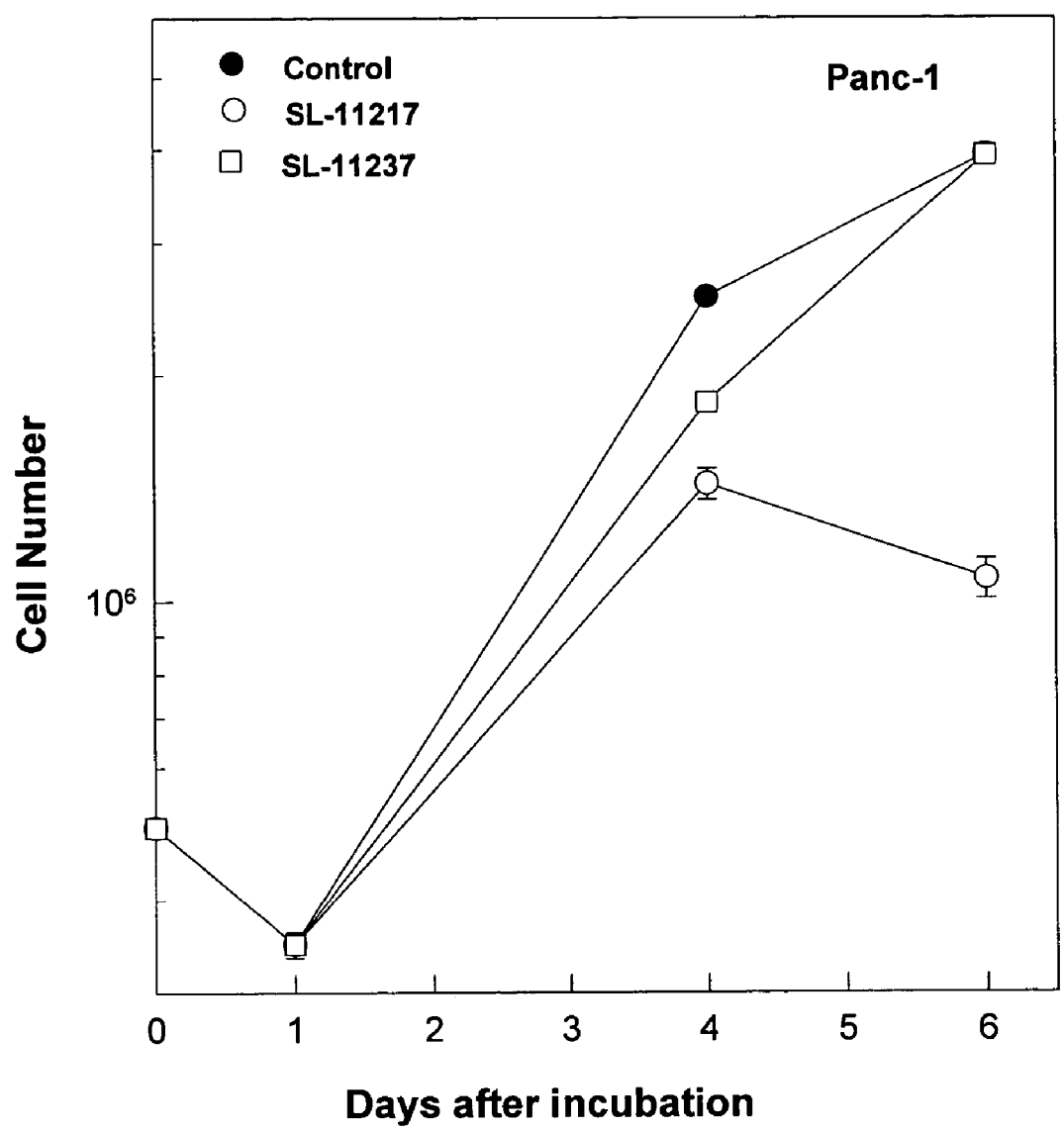

FIG. 11. is a graph depicting the in vitro effects of 10 µM SL-11217 and SL-11237 on the growth of cultured human pancreatic cancer cells Panc1.

Figure 12:
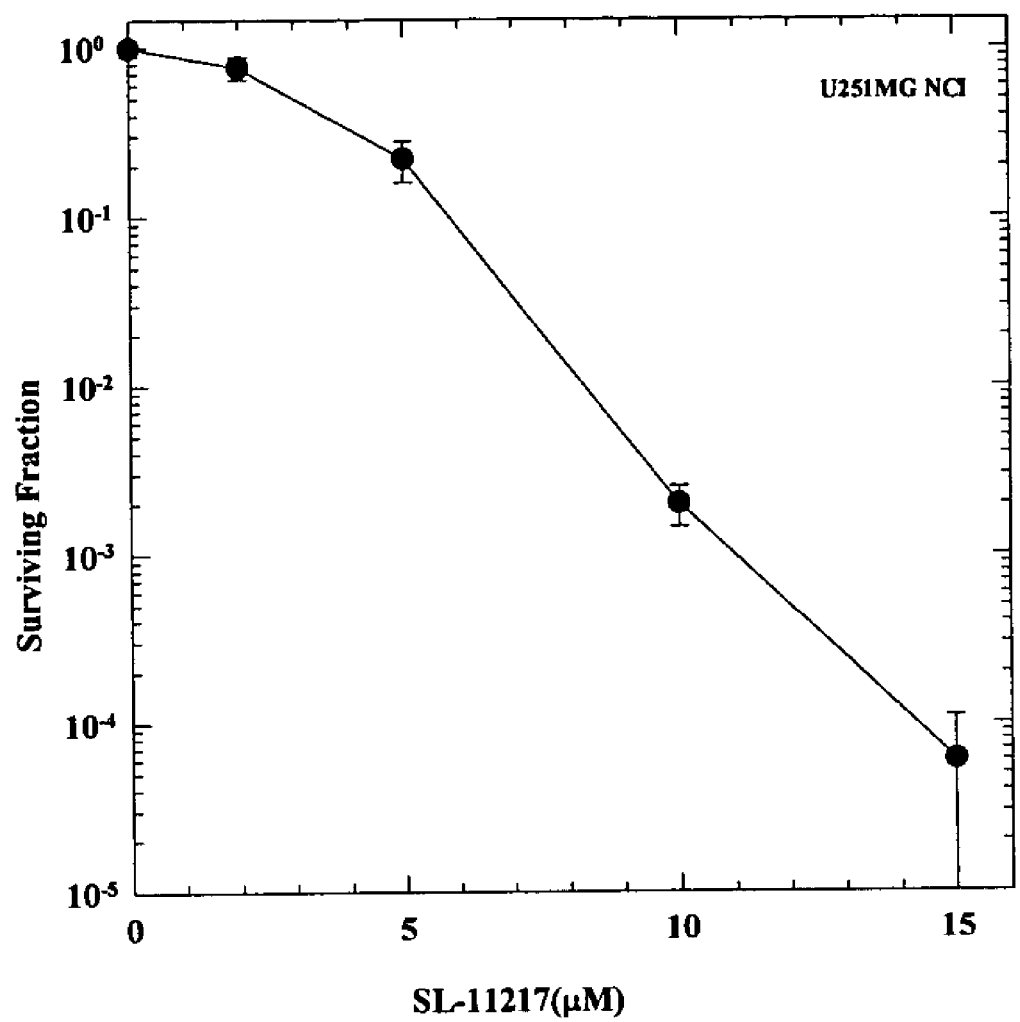

FIG. 12. is a graph depicting the in vitro effects of increasing concentrations of SL-11217 on the survival of cultured human brain tumor cells U251MG NCI after 3 days of treatment.

Figure 13:
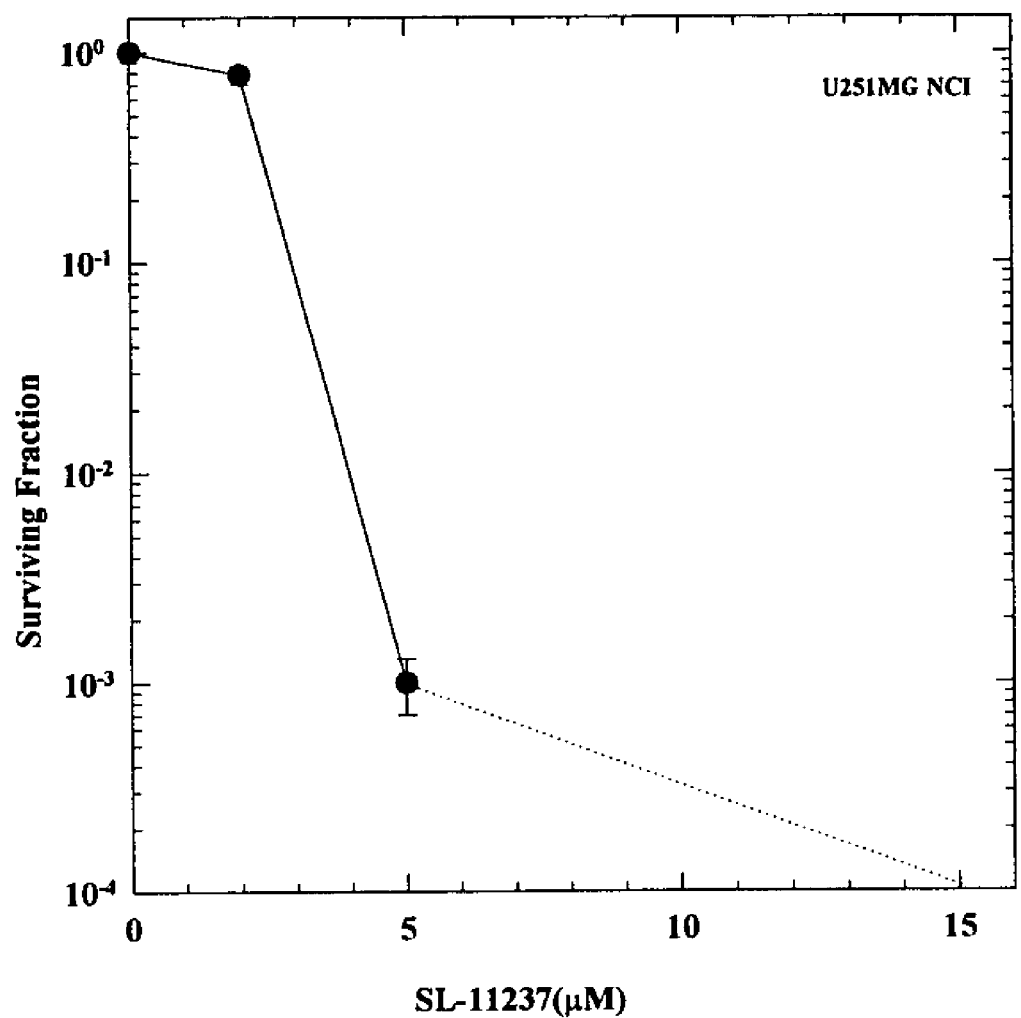

FIG. 13. is a graph depicting the in vitro effects of increasing concentrations of SL-11237 on the survival of cultured human brain tumor cells U251MG NCI after 3 days of treatment.

FIG. 14 depicts the effects of SL-11237 via oral administration. Male athymic nude mice were given subcutaneous injections of 0.75×10$^6$ DU145 cells on Day 0. Beginning on Day 10, mice were treated once weekly for 3 weeks with acidified water, 100 mg/kg, or 500 mg/kg of SL-11237 via oral gavage at 10 ml/kg dosing volume (the third treatment was actually 400 mg/kg in the high dose group). The top panel depicts average tumor volume in the mice. The bottom panel depicts average body weight of the mice.

DETAILED DESCRIPTION OF THE INVENTION

The invention is directed to various novel porphyrin-polyamine conjugate compounds and compositions containing them as described herein. The invention includes all salts of the compounds described herein. Particularly preferred are pharmaceutically acceptable salts. Pharmaceutically acceptable salts are those salts which retain the biological activity of the free bases and which are not biologically or otherwise undesirable. The desired salt may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of the compounds with amino acids, such as aspartate salts and glutamate salts, can also be prepared.

The invention also includes all stereoisomers of the compounds, including diastereomers and enantiomers, as well as mixtures of stereoisomers, including, but not limited to, racemic mixtures. Unless stereochemistry is explicitly indicated in a structure, the structure is intended to embrace all possible stereoisomers of the compound depicted.

The term "alkyl" refers to saturated aliphatic groups including straight-chain, branched-chain, cyclic groups, and combinations thereof, having the number of carbon atoms specified, or if no number is specified, having up to 12 carbon atoms. "Straight-chain alkyl" or "linear alkyl" groups refers to alkyl groups that are neither cyclic nor branched, commonly designated as "n-alkyl" groups. Examples of alkyl groups include, but are not limited to, groups such as methyl, ethyl, n-propyl, isopropyl, butyl, n-butyl, isobutyl, sec-butyl, t-butyl, pentyl, n-pentyl, hexyl, heptyl, octyl, nonyl, decyl, undecyl, dodecyl, neopentyl, cyclopropyl, cyclobutyl, cyclopentyl, cyclohexyl, and adamantyl. Cyclic groups can consist of one ring, including, but not limited to, groups such as cycloheptyl, or multiple fused rings, including, but not limited to, groups such as adamantyl or norbornyl. Preferred subsets of alkyl groups include $C_1$–$C_{12}$, $C_1$–$C_{10}$, $C_1$–$C_8$, $C_1$–$C_6$, $C_1$–$C_4$, $C_1$–$C_2$, $C_3$–$C_4$, $C_3$, and $C_4$ alkyl groups.

"Substituted alkyl" refers to alkyl groups substituted with one or more substituents including, but not limited to, groups such as halogen (fluoro, chloro, bromo, and iodo), alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. Examples of substituted alkyl groups include, but are not limited to, —$CF_3$, —$CF_2$—$CF_3$, and other perfluoro and perhalo groups.

"Hydroxyalkyl" specifically refers to alkyl groups having the number of carbon atoms specified substituted with one —OH group. Thus, "$C_3$ linear hydroxyalkyl" refers to —$CH_2CH_2CHOH$—, —$CH_2CHOHCH_2$—, and —$CHOHCH_2CH_2$—.

The term "alkenyl" refers to unsaturated aliphatic groups including straight-chain (linear), branched-chain, cyclic groups, and combinations thereof, having the number of carbon atoms specified, or if no number is specified, having up to 12 carbon atoms, which contain at least one double bond (—C=C—). Examples of alkenyl groups include, but are not limited to, —$CH_2$—CH=CH—$CH_3$; and —$CH_2$—$CH_2$-cyclohexenyl, where the ethyl group can be attached to the cyclohexenyl moiety at any available carbon valence. The term "alkynyl" refers to unsaturated aliphatic groups including straight-chain (linear), branched-chain, cyclic groups, and combinations thereof, having the number of carbon atoms specified, or if no number is specified, having up to 12 carbon atoms, which contain at least one triple bond (—C≡C—). "Hydrocarbon chain" or "hydrocarbyl" refers to any combination of straight-chain, branched-chain, or cyclic alkyl, alkenyl, or alkynyl groups, and any combination thereof. "Substituted alkenyl," "substituted alkynyl," and "substituted hydrocarbon chain" or "substituted hydrocarbyl" refer to the respective group substituted with one or more substituents, including, but not limited to, groups such as halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group.

For all of the foregoing definitions, preferred subsets of the groups include $C_1$–$C_{12}$, $C_1$–$C_{10}$, $C_1$–$C_8$, $C_1$–$C_6$, $C_1$–$C_4$, $C_1$–$C_2$ (when chemically possible), $C_3$–$C_4$, $C_3$, and $C_4$ groups.

"Aryl" or "Ar" refers to an aromatic carbocyclic group having a single ring (including, but not limited to, groups such as phenyl) or multiple condensed rings (including, but not limited to, groups such as naphthyl or anthryl), and includes both unsubstituted and substituted aryl groups. "Substituted aryls" refers to aryls substituted with one or more substituents, including, but not limited to, groups such as alkyl, alkenyl, alkynyl, hydrocarbon chains, halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group.

"Heteroalkyl," "heteroalkenyl," and "heteroalkynyl" refer to alkyl, alkenyl, and alkynyl groups, respectively, that contain the number of carbon atoms specified (or if no number is specified, having up to 12 carbon atoms) which contain one or more heteroatoms as part of the main, branched, or cyclic chains in the group. Heteroatoms include, but are not limited to, N, S, O, and P; N and O are preferred. Heteroalkyl, heteroalkenyl, and heteroalkynyl groups may be attached to the remainder of the molecule either at a heteroatom (if a valence is available) or at a carbon atom. Examples of heteroalkyl groups include, but are not limited to, groups such as —O—CH$_3$, —CH$_2$—O—CH$_3$, —CH$_2$—CH$_2$—O—CH$_3$, —S—CH$_2$—CH$_2$—CH$_3$, —CH$_2$—CH(CH$_3$)—S—CH$_3$, —CH$_2$—CH$_2$—NH—CH$_2$—CH$_2$—, 1-ethyl-6-propylpiperidino, 2-ethylthiophenyl, and morpholino. Examples of heteroalkenyl groups include, but are not limited to, groups such as —CH═CH—NH—CH(CH$_3$)—CH$_2$—. "Heteroaryl" or "HetAr" refers to an aromatic carbocyclic group having a single ring (including, but not limited to, examples such as pyridyl, thiophene, or furyl) or multiple condensed rings (including, but not limited to, examples such as imidazolyl, indolizinyl or benzothienyl) and having at least one hetero atom, including, but not limited to, heteroatoms such as N, O, P, or S, within the ring. Unless otherwise specified, heteroalkyl, heteroalkenyl, heteroalkynyl, and heteroaryl groups have between one and five heteroatoms and between one and twelve carbon atoms. "Substituted heteroalkyl," "substituted heteroalkenyl," "substituted heteroalkynyl," and "substituted heteroaryl" groups refer to heteroalkyl, heteroalkenyl, heteroalkynyl, and heteroaryl groups substituted with one or more substituents, including, but not limited to, groups such as alkyl, alkenyl, alkynyl, benzyl, hydrocarbon chains, halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. Examples of such substituted heteroalkyl groups include, but are not limited to, piperazine, substituted at a nitrogen or carbon by a phenyl or benzyl group, and attached to the remainder of the molecule by any available valence on a carbon or nitrogen, —NH—SO$_2$-phenyl, —NH—(C═O)O-alkyl, —NH—(C═O)O-alkyl-aryl, and —NH—(C═O)-alkyl. If chemically possible, the heteroatom(s) as well as the carbon atoms of the group can be substituted. The heteroatom(s) can also be in oxidized form, if chemically possible.

The term "alkylaryl" refers to an alkyl group having the number of carbon atoms designated, appended to one, two, or three aryl groups.

The term "alkoxy" as used herein refers to an alkyl, alkenyl, alkynyl, or hydrocarbon chain linked to an oxygen atom and having the number of carbon atoms specified, or if no number is specified, having up to 12 carbon atoms. Examples of alkoxy groups include, but are not limited to, groups such as methoxy, ethoxy, and t-butoxy.

The term "alkanoate" as used herein refers to an ionized carboxylic acid group, such as acetate ($CH_3C(═O)$—$O^{(-1)}$), propionate ($CH_3CH_2C(═O)$—$O^{(-1)}$), and the like. "Alkyl alkanoate" refers to a carboxylic acid esterified with an alkoxy group, such as ethyl acetate ($CH_3C(═O)$—$O$—$CH_2CH_3$). "ω-haloalkyl alkanoate" refers to an alkyl alkanoate bearing a halogen atom on the alkanoate carbon atom furthest from the carboxyl group; thus, ethyl ω-bromo propionate refers to ethyl 3-bromopropionate, methyl ω-chloro n-butanoate refers to methyl 4-chloro n-butanoate, etc.

The terms "halo" and "halogen" as used herein refer to Cl, Br, F or I substituents.

"Protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups can be found in Greene et al. (1991) *Protective Groups in Organic Synthesis*, 2nd Ed. (John Wiley & Sons, Inc., New York). Amino protecting groups include, but are not limited to, mesitylenesulfonyl (Mes), benzyloxycarbonyl (CBz or Z), t-butyloxycarbonyl (Boc), t-butyldimethylsilyl (TBDIMS or TBDMS), 9-fluorenylmethyloxycarbonyl (Fmoc), tosyl, benzenesulfonyl, 2-pyridyl sulfonyl, or suitable photolabile protecting groups such as 6-nitroveratryloxy carbonyl (Nvoc), nitropiperonyl, pyrenylmethoxycarbonyl, nitrobenzyl, dimethyl dimethoxybenzil, 5-bromo-7-nitroindolinyl, and the like. Hydroxyl protecting groups include, but are not limited to, Fmoc, TBDIMS, photolabile protecting groups (such as nitroveratryl oxymethyl ether (Nvom)), Mom (methoxy methyl ether), and Mem (methoxy ethoxy methyl ether), NPEOC (4-nitrophenethyloxycarbonyl) and NPEOM (4-nitrophenethyloxymethyloxycarbonyl).

Synthesis of Porphyrin-Polyamine Conjugates: Overview

Syntheses are described with reference to the schemes below. The synthesis of SL-11211 (Scheme 1) started with acetal 1 that was protected by mesitylene sulfonation to give 2. Alkylation of the known triamide 3 with 4-bromobutyronitrile following the procedure described previously (see Examples), reduction of the resulting nitrile and mesitylene sulfonation of the free amine gave octaamide 4. Treatment of 4 with 1,4-dibromobutane gave 5, that was then condensed with 2 to afford 6. Cleavage of the acetal residue of 6 resulted in the aldehyde 7, that was subjected to reductive amination with ethylamine to give 8. The amine was then condensed with mesoporhyrin dihdrochloride to the porphyrin diamide 9; deprotection of the amino residues of 9 gave SL-11211.

The synthesis of SL-11233 (Scheme 2) started with the known triamide 10 that was alkylated with 1,4-dibromobutane to give 11. The latter is condensed with 2 to give 12, the acetal cleaved to aldehyde 13, and the latter reductively aminated to 14. Condensation of 14 with deuteroporphyrin IX 2,4-disulfonic acid gave 15. Cleavage of the protecting groups in 15 allowed the synthesis of SL-11233.

The synthesis of SL-11235 started with the condensation of 8 and deuteroporphyrin IX-2,4-disulfonate to give 16 (Scheme 3). Deprotection of the amino residues gave SL-11235 eicosahydrobromide.

The synthesis of SL-11236 started with the condensation of 8 and N-methylmesoporphyrin IX to give 17, that was then deprotected to give SL-11236 eicosahydrobromide (Scheme 3).

The synthesis of SL-11237 started with the previously described cyclic amine 18 (patent cyclic polyamines) that was condensed with mesoporphyrin IX. dihydrochloride to give SL-11237 (Scheme 3).

The synthesis of SL-11217 (Scheme 4) started with the known cyclopropyl derivative 19, that was hydrolyzed to the acid and the latter transformed into its chloride 20. Condensation of 20 with a protected N-ethyl 1,4-diaminobutane gave 21, that was reduced with diborane and then acylated with mesitylenesulfonyl chloride to give 22. Alkylation of 22 with dibromobutane in the presence of sodium iodide gave 23, that was condensed with ethylamine to give 24.

Condensation of 24 with mesoporphyrin IX dihydrochloride gave 25, deprotection of the amino residues gave SL-11217 hydrobromide.

The synthesis of SL-11209 started with the known amine 26 that was alkylated with the benzyl ether of 4-bromobutanol to give 27 (Scheme 5). Hydrolysis of the benzyl ether gave the alcohol 28, the alcohol was protected by reaction with t-butyloxycarbonyl anhydride to give 29, and the latter oxidized to the aldehyde 30. Reductive amination of 30 gave 31. In tandem, reduction of the diester of mesoporphyrin gave the dialdehyde 32. Condensation of 32 with 31, followed by acid deprotection of the amino residues gave SL-11209.

The synthesis of SL-11210 started with the known nitrile 33 that was reduced to the amine and the latter condensed with 32 following a reductive amination procedure (Scheme 6). Deprotection of the amino residues gave SL-11210.

Reductive amination procedures allowed the condensation of 18 and aldehyde 32 that gave SL-11257 (Scheme 7)

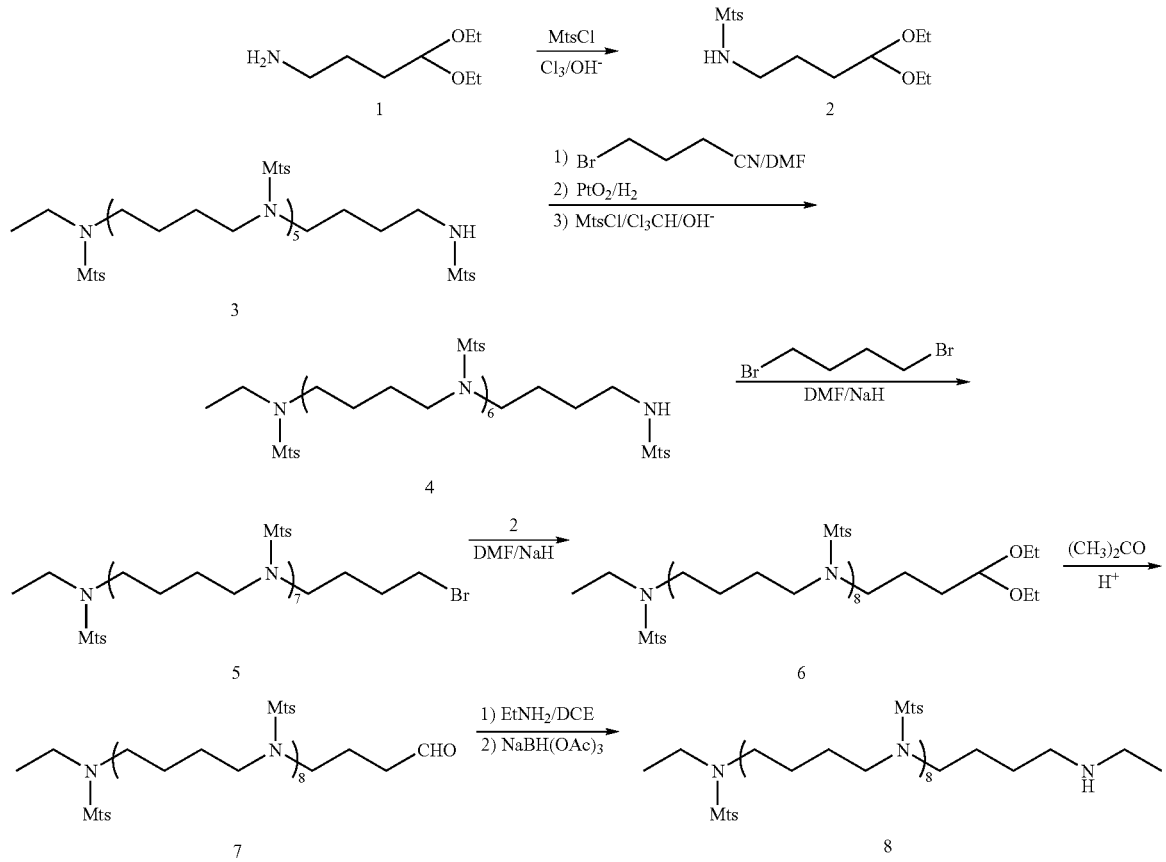

SCHEME 1

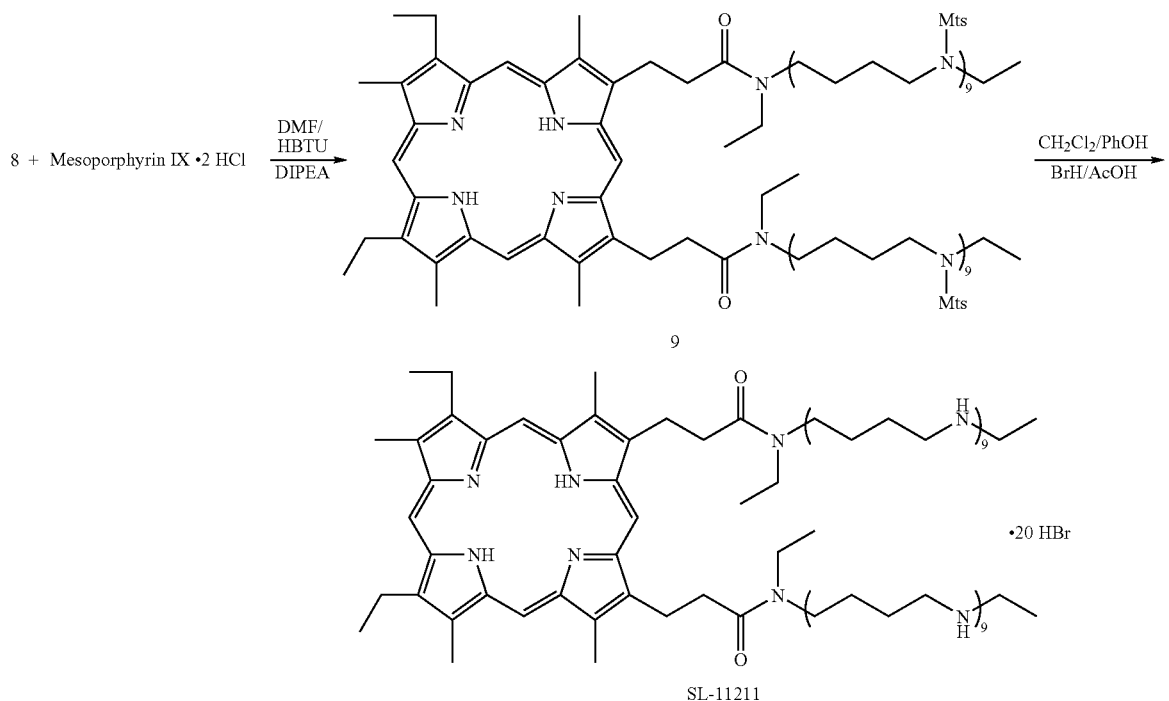
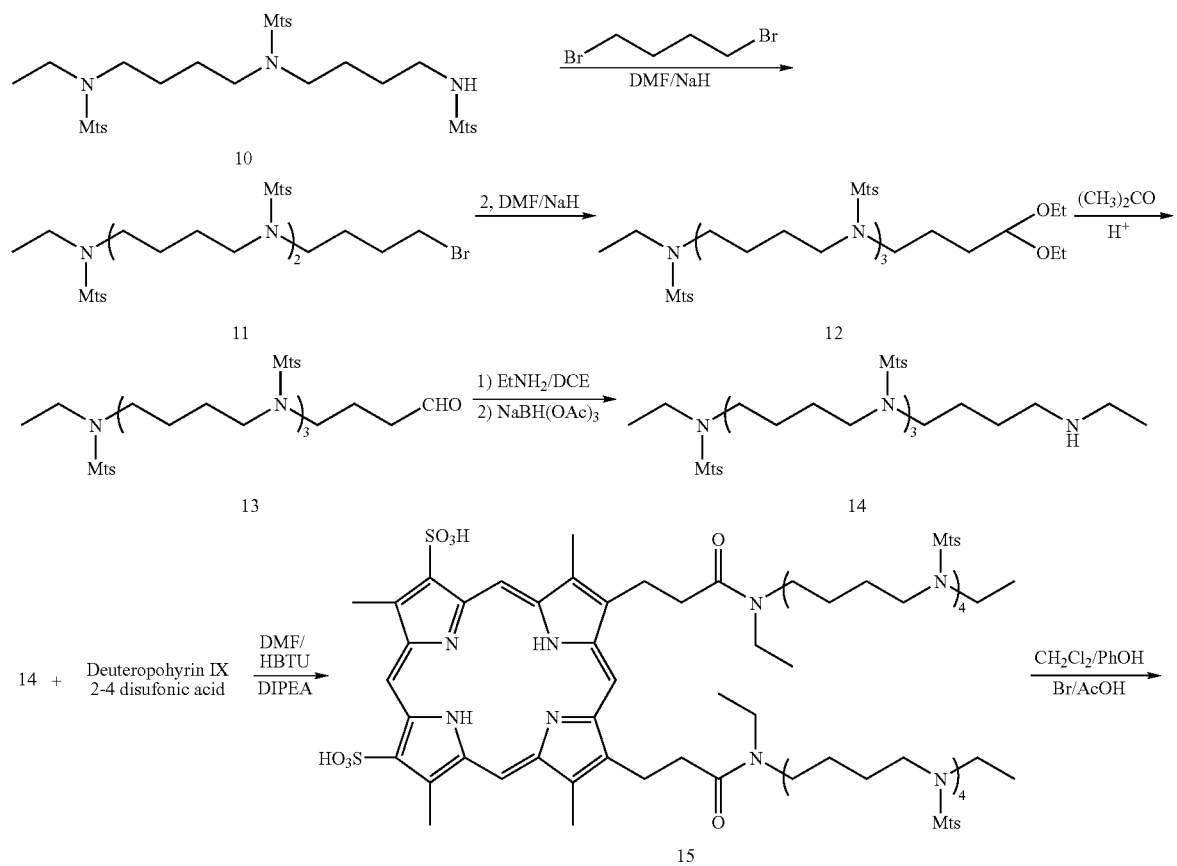

-continued
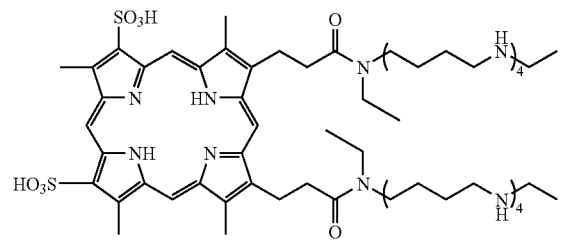
SL-11233
SCHEME 3
8 + Deuteroporpyrin IX 2-4 disulfonic acid →(DMF/HBTU, DIPEA)→
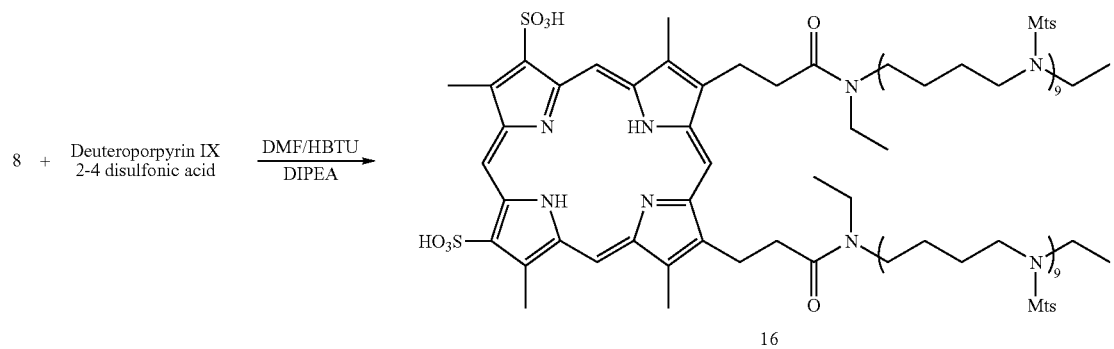
16
16 →(CH₂Cl₂/PhOH, BrH/AcOH)→
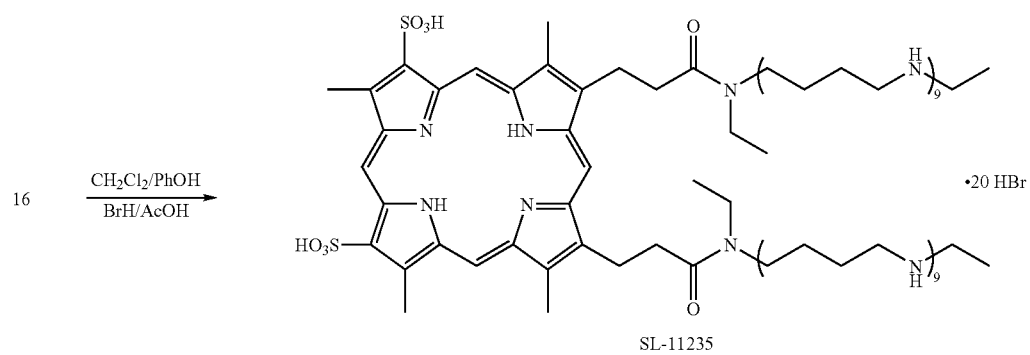
SL-11235 ·20 HBr
8 + N-methylmesoporphyrin IX →(DMF/HBTU, DIPEA)→
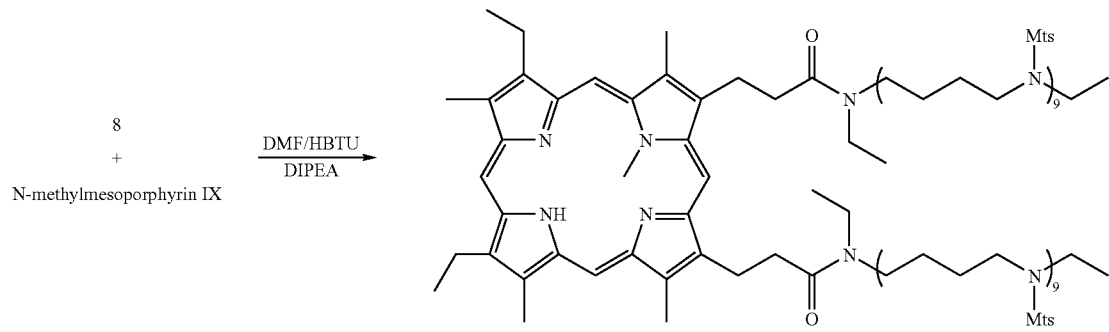
17

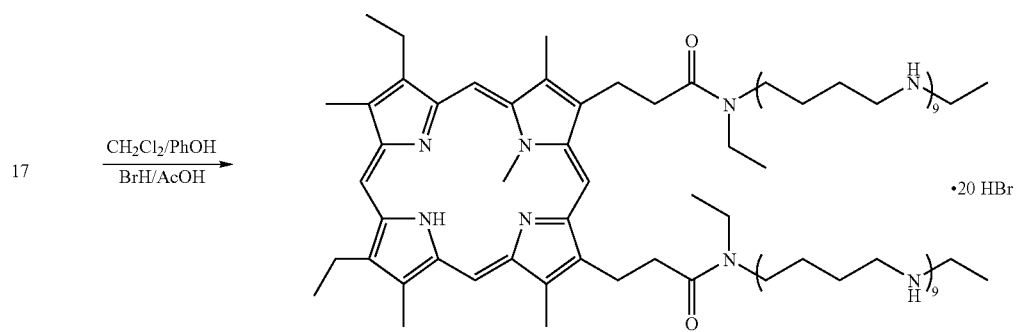
SL-11236
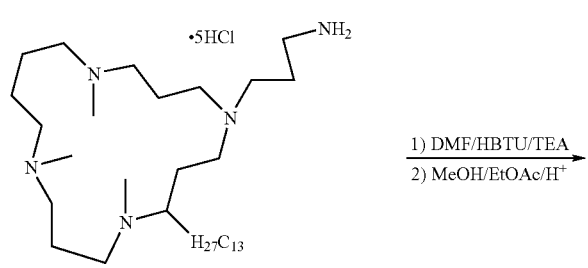
18 +
Mesoporphyrin IX •2 HCl
1) DMF/HBTU/TEA
2) MeOH/EtOAc/H⁺
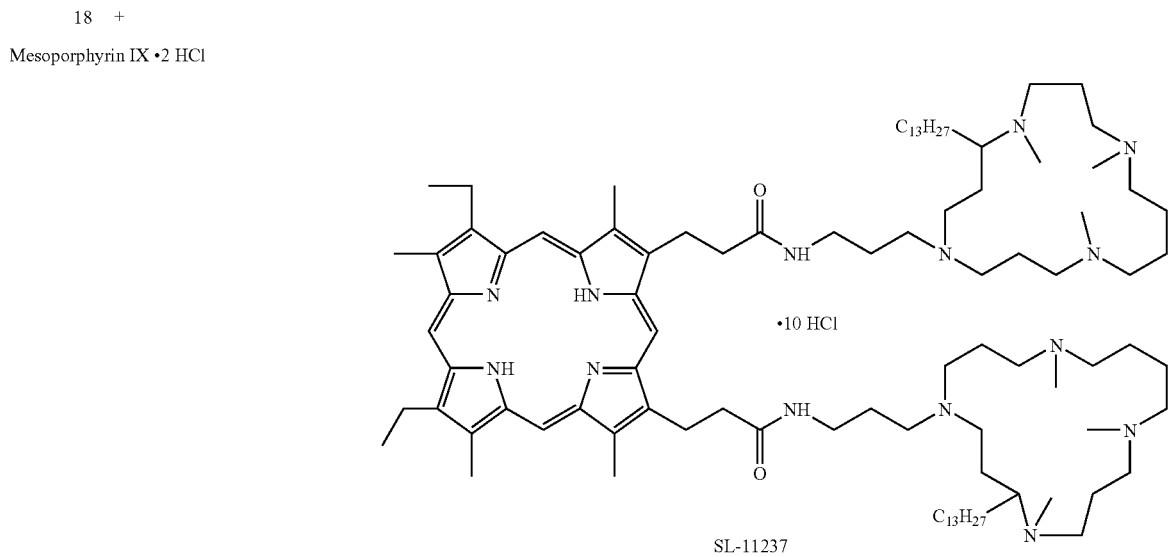
SL-11237
SCHEME 4
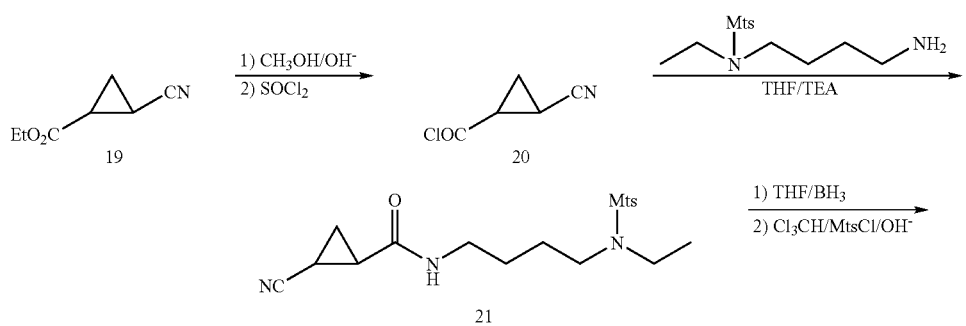

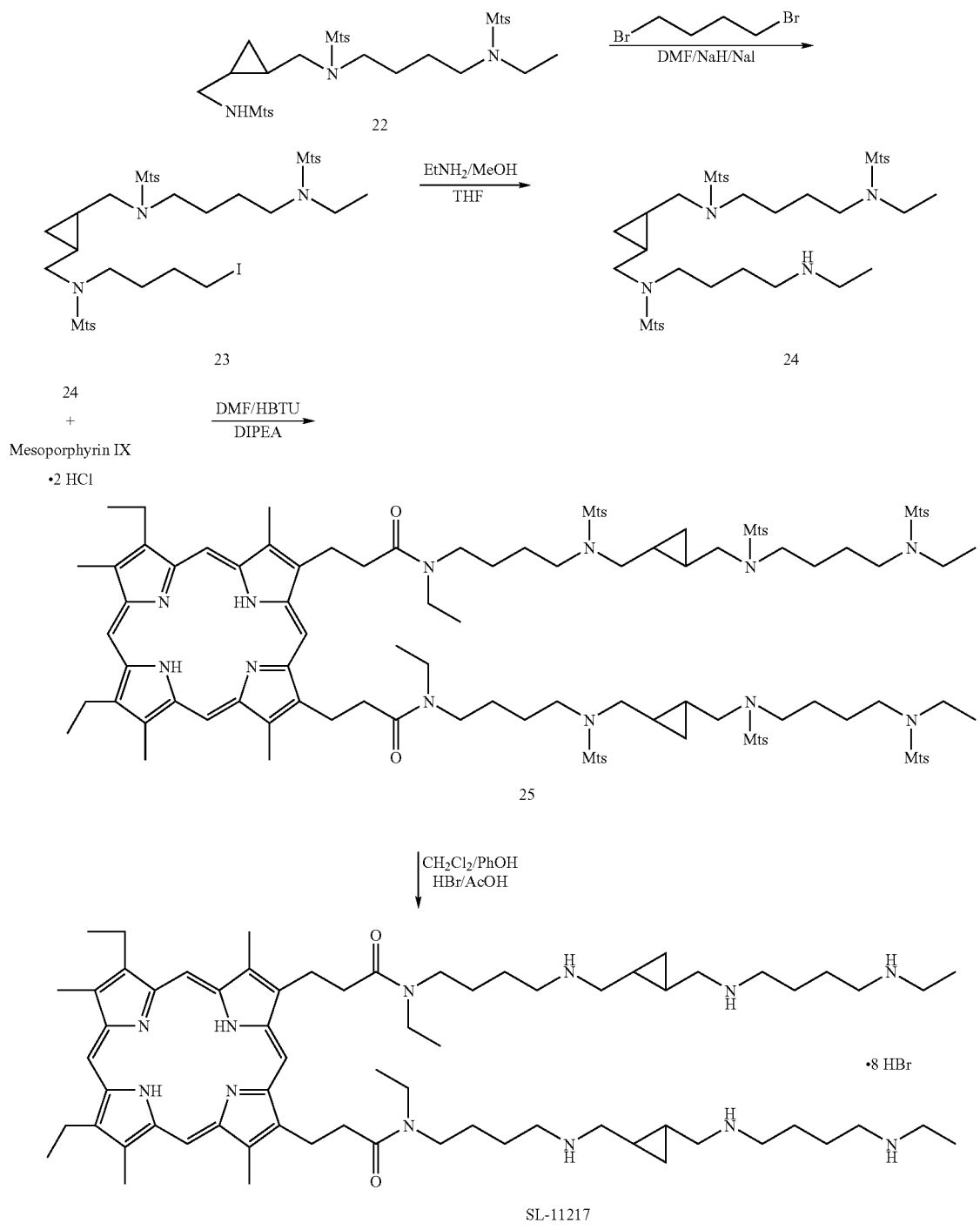
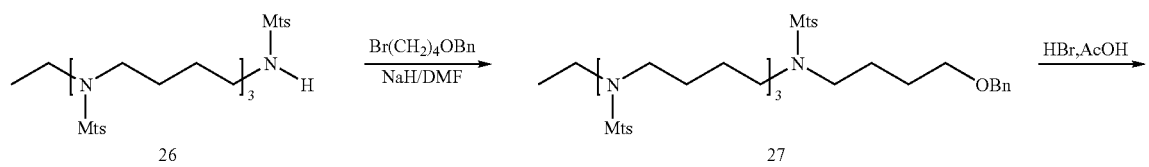
SCHEME 5

-continued
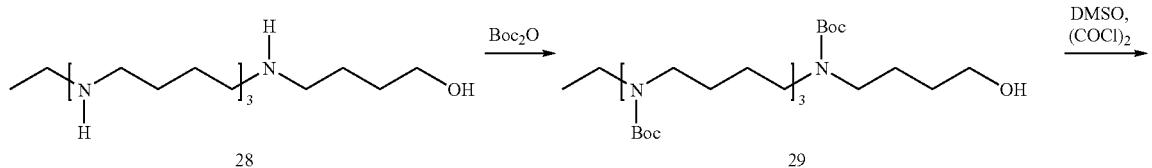
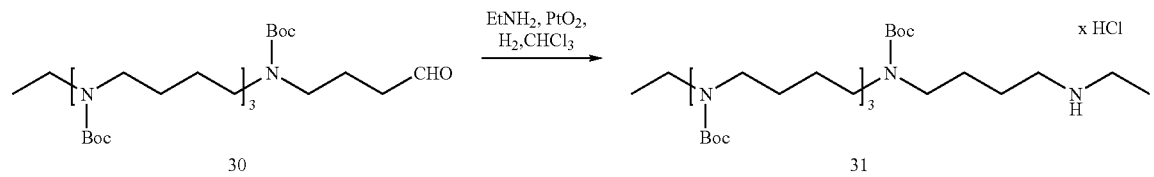
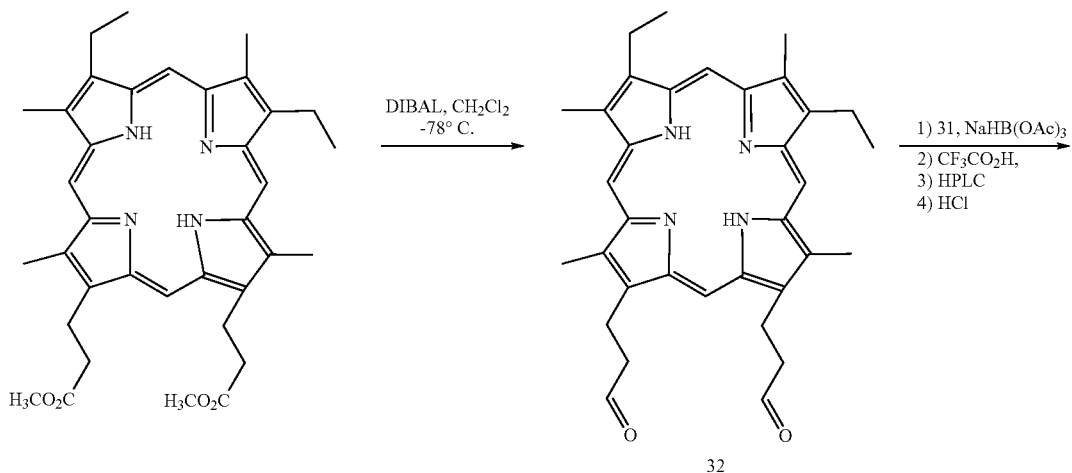
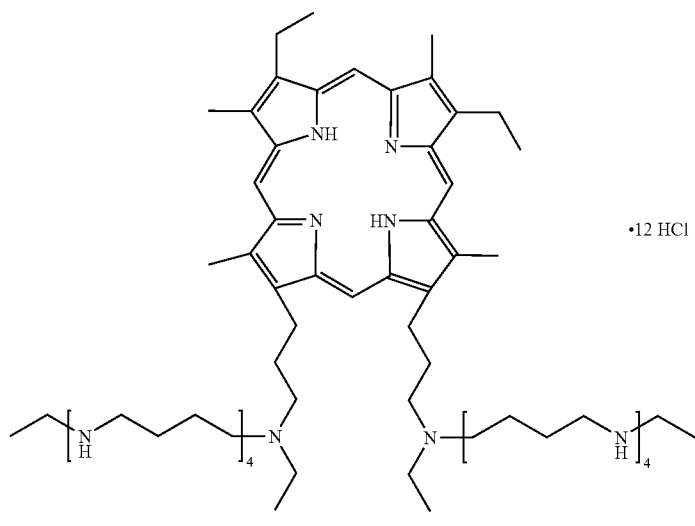
SL11209

SCHEME 6
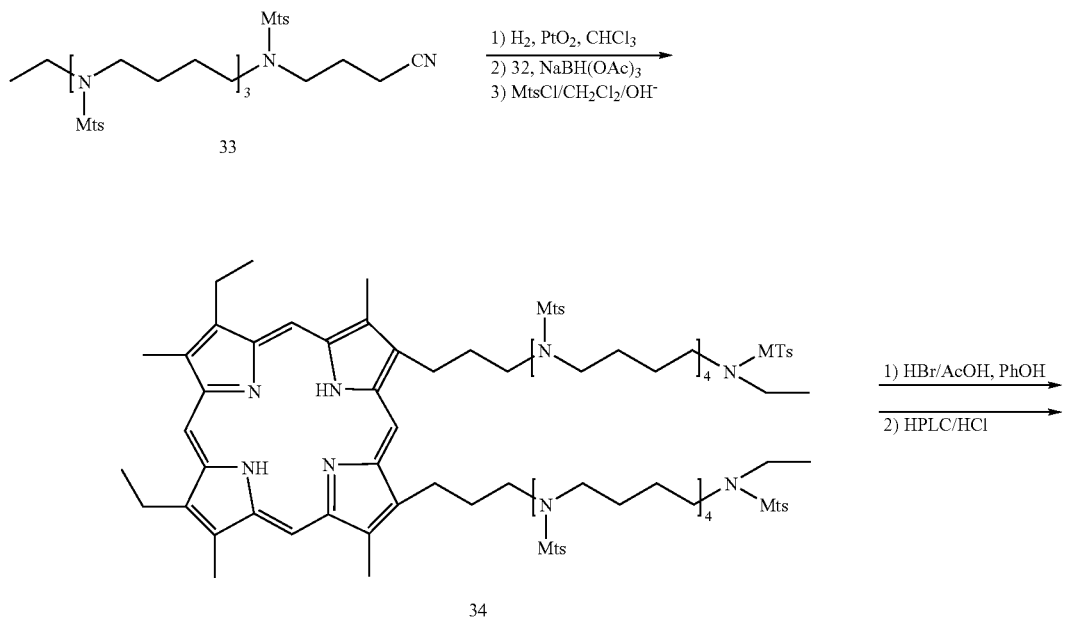
SCHEME 7
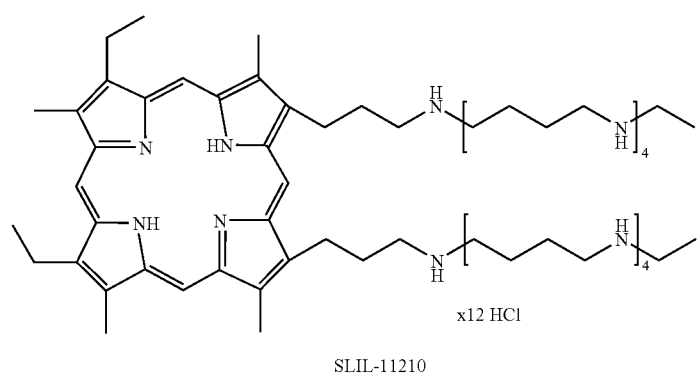
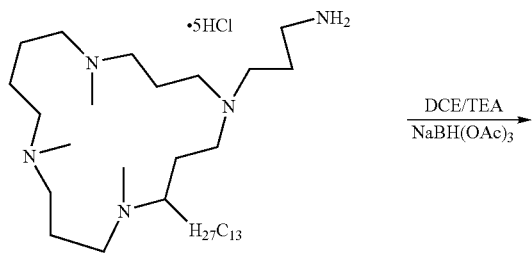

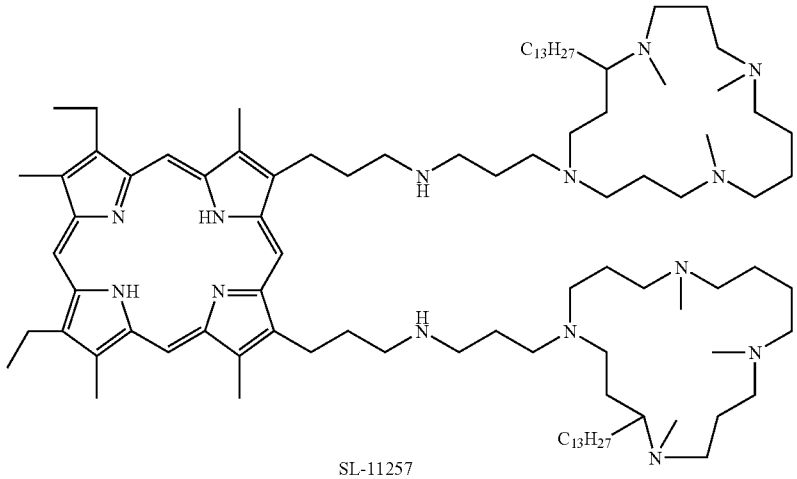

SL-11257

Therapeutic Use of Porphyrin-Polyamine Conjugate Compounds

Porphyrin-polyamine conjugate compounds of the present invention are useful for treatment of a variety of diseases caused by uncontrolled proliferation of cells, including cancer, particularly prostate cancer. The compounds are used to treat mammals, preferably humans. "Treating" a disease using a porphyrin-polyamine conjugate compound of the invention is defined as administering one or more porphyrin-polyamine conjugate compounds of the invention, with or without additional therapeutic agents, in order to prevent, reduce, or eliminate either the disease or the symptoms of the disease, or to retard the progression of the disease or of symptoms of the disease. "Therapeutic use" of the porphyrin-polyamine conjugate compounds of the invention is defined as using one or more porphyrin-polyamine conjugate compounds of the invention to treat a disease, as defined above.

In order to evaluate the efficacy of a particular porphyrin-polyamine conjugate compound for a particular medicinal application, the compounds can be first tested against appropriately chosen test cells in vitro. In a non-limiting example, porphyrin-polyamine conjugate compounds can be tested against tumor cells, for example, prostate tumor cells. Exemplary experiments can utilize cell lines capable of growing in culture as well as in vivo in athymic nude mice, such as LNCaP. Horoszewicz et al. (1983) Cancer Res. 43:1809–1818. Culturing and treatment of carcinoma cell lines, cell cycle and cell death determinations based on flow cytometry; enzyme assays including ODC, SAMDC and SSAT activities; and high pressure liquid chromatography detection and quantitation of natural polyamines and polyamine analogs are described in the art, for example, Mi et al. (1998) Prostate 34:51–60; Kramer et al. (1997) Cancer Res. 57:5521–27; and Kramer et al. (1995) J. Biol. Chem. 270:2124–2132. Evaluations can also be made of the effects of the porphyrin-polyamine conjugate compound on cell growth and metabolism.

Analysis begins with $IC_{50}$ determinations based on dose-response curves ranging from 0.1 to 1000 μM performed at 72 hr. From these studies, conditions can be defined which produce about 50% growth inhibition and used to: (a) follow time-dependence of growth inhibition for up to 6 days, with particular attention to decreases in cell number, which may indicate drug-induced cell death; (b) characterize porphyrin-polyamine conjugate compound effects on cell cycle progression and cell death using flow cytometry (analysis to be performed on attached and detached cells); (c) examine porphyrin-polyamine conjugate compound effects on cellular metabolic parameters. Porphyrin-polyamine conjugate compound effects can be normalized to intracellular concentrations (by HPLC analysis), which also provide an indication of their relative ability to penetrate cells. Marked differences in porphyrin-polyamine conjugate compound uptake can be further characterized by studying the compound's ability to utilize and regulate the polyamine transporter, as assessed by competition studies using radiolabeled spermidine, as previously described in Mi et al. (1998). Porphyrin-polyamine conjugate compounds could also enter the cells by a diffusion mechanism.

In Vivo Testing of Porphyrin-Polyamine Conjugate Compounds

Porphyrin-polyamine conjugate compounds found to have potent anti-proliferative activity in vitro towards cultured carcinoma cells can be evaluated in in vivo model systems. The first goal is to determine the relative toxicity of the compounds in non-tumor-bearing animals, such as DBA/2 mice. Groups of three animals each can be injected intraperitoneally with increasing concentrations of a porphyrin-polyamine conjugate compound, beginning at, for example, 10 mg/kg. Toxicity as indicated by morbidity is closely monitored over the first 24 hr. A well-characterized polyamine analog compound, such as BE-333, can be used as an internal standard in these studies, since a data base has already been established regarding acute toxicity via a single dose treatment relative to chronic toxicity via a daily×5 d schedule. Thus, in the case of porphyrin-polyamine conjugate compounds, single dose toxicity relative to BE-333 is used to project the range of doses to be used on a daily×5 d schedule. The toxicity of the porphyrin-polyamine conjugate compound can also be tested versus the free polyamine compound, that is, versus the same polyamine which is present in the porphyrin-polyamine conjugate compound but without a conjugated porphyrin.

After the highest tolerated dosage on a daily×5 d schedule is deduced, antitumor activity is determined. Typically, tumors can be subcutaneously implanted into nude athymic mice by trocar and allowed to reach 100–200 mm³ before initiating treatment by intraperitoneal injection daily×5 d. Most porphyrin-polyamine conjugate compounds can be given in a range between 10 and 200 mg/kg. Porphyrin-polyamine conjugate compounds can be evaluated at three treatment dosages with 10–15 animals per group (a minimum of three from each can be used for pharmacodynamic studies, described below). Mice can be monitored and weighed twice weekly to determine tumor size and toxicity. Tumor size is determined by multi-directional measurement from which volume in $mm^3$ is calculated. Tumors can be followed until median tumor volume of each group reaches 1500 $mm^3$ (i.e., 20% of body weight), at which time the animals can be sacrificed. Although the initial anti-tumor studies focuses on a daily×5 d schedule, constant infusion can be performed via Alzet pump delivery for 5 days since this schedule dramatically improves the anti-tumor activity of BE-333 against A549 human large cell hung carcinoma. Sharma et al. (1997) *Clin. Cancer Res.* 3:1239–1244. In addition to assessing anti-tumor activity, free porphyrin-polyamine conjugate compound levels and free polyamine levels in tumor and normal tissues can be determined in test animals.

Methods of Administration of Porphyrin-Polyamine Conjugate Compounds

The porphyrin-polyamine conjugate compounds of the present invention can be administered to a mammalian, preferably human, subject via any route known in the art, including, but not limited to, those disclosed herein. Methods of administration include but are not limited to, oral, intravenous, intraarterial, intratumoral, intramuscular, topical, inhalation, subcutaneous, intraperitoneal, gastrointestinal, and directly to a specific or affected organ. The porphyrin-polyamine conjugate compounds described herein are administratable in the form of tablets, pills, powder mixtures, capsules, granules, injectables, creams, solutions, suppositories, emulsions, dispersions, food premixes, and in other suitable forms. The compounds can also be administered in liposome formulations. The compounds can also be administered as prodrugs, where the prodrug undergoes transformation in the treated subject to a form which is therapeutically effective. Additional methods of administration are known in the art.

The pharmaceutical dosage form which contains the compounds described herein is conveniently admixed with a non-toxic pharmaceutical organic carrier or a non-toxic pharmaceutical inorganic carrier. Typical pharmaceutically-acceptable carriers include, for example, mannitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid, and other conventionally employed acceptable carriers. The pharmaceutical dosage form can also contain non-toxic auxiliary substances such as emulsifying, preserving, or wetting agents, and the like. A suitable carrier is one which does not cause an intolerable side effect, but which allows the novel porphyrin-polyamine conjugate compound(s) to retain its pharmacological activity in the body. Formulations for parenteral and nonparenteral drug delivery are known in the art and are set forth in *Remington's Pharmaceutical Sciences,* 18th Edition, Mack Publishing (1990). Solid forms, such as tablets, capsules and powders, can be fabricated using conventional tableting and capsule-filling machinery, which is well known in the art. Solid dosage forms, including tablets and capsules for oral administration in unit dose presentation form, can contain any number of additional non-active ingredients known to the art, including such conventional additives as excipients; desiccants; colorants; binding agents, for example syrup, acacia, gelatin, sorbitol, tragacanth, or polyvinylpyrollidone; fillers, for example lactose, sugar, maize-starch, calcium phosphate, sorbitol or glycine; tableting lubricants, for example magnesium stearate, talc, polyethylene glycol or silica; disintegrants, for example potato starch; or acceptable wetting agents such as sodium lauryl sulfate. The tablets can be coated according to methods well known in standard pharmaceutical practice. Liquid forms for ingestion can be formulated using known liquid carriers, including aqueous and non-aqueous carriers, suspensions, oil-in-water and/or water-in-oil emulsions, and the like. Liquid formulations can also contain any number of additional non-active ingredients, including colorants, fragrance, flavorings, viscosity modifiers, preservatives, stabilizers, and the like. For parenteral administration, porphyrin-polyamine conjugate compounds can be administered as injectable dosages of a solution or suspension of the compound in a physiologically acceptable diluent or sterile liquid carrier such as water or oil, with or without additional surfactants or adjuvants. An illustrative list of carrier oils would include animal and vegetable oils (e.g., peanut oil, soy bean oil), petroleum-derived oils (e.g., mineral oil), and synthetic oils. In general, for injectable unit doses, water, saline, aqueous dextrose and related sugar solutions, and ethanol and glycol solutions such as propylene glycol or polyethylene glycol are preferred liquid carriers. The pharmaceutical unit dosage chosen is preferably fabricated and administered to provide a final concentration of drug at the point of contact with the cancer cell of from 1 µM to 10 mM. More preferred is a concentration of from 1 to 100 µM. The optimal effective concentration of porphyrin-polyamine conjugate compounds can be determined empirically and will depend on the type and severity of the disease, route of administration, disease progression and health and mass or body area of the patient. Such determinations are within the skill of one in the art. Porphyrin-polyamine conjugate compounds can be administered as the sole active ingredient, or can be administered in combination with another active ingredient, including, but not limited to, cytotoxic agents, antibiotics, antimetabolites, nitrosourea, vinca alkaloids, polypeptides, antibodies, cytokines, etc.

EXAMPLES

The following examples are provided to illustrate the invention, and are not intended to limit the invention in any manner.

Synthesis of SL-11211

Example 1

N-Mesitylenesulfonyl 4-aminobutyraldehyde diethyl acetal 2

Amine 1 (Aldrich) (3.5 g, 21.7 mol) was dissolved in a mixture of chloroform (30 ml) and 1N sodium hydroxide (24 ml) and 15 ml of mesitylenesulfonyl chloride dissolved in 15 ml of chloroform were added at 5° C. The mixture was stirred for 2 h, the reaction mixture was then diluted with chloroform (50 ml), the organic layer was separated, washed with a saturated solution of ammonium chloride, dried ($Na_2SO_4$), and evaporated to dryness. The residual oil crys tallized after drying and was used in the next step without further purification; 7.0 g (95%) of 2 were obtained; $^1$HNMR (CDCl$_3$): ppm 1.15(t,6H), 1.55 (m,4H), 2.30 (s, 3H), 2.65 (s, 6H), 2.95 (q, 2H), 3.40–3.55 (m, 4H), 4.40 (t, 1H), 4.90 (t, 1H), 6.95 (s, 2H); $^{13}$CNMR (CDCl$_3$): ppm 15.19, 20.80, 22.85, 24.55, 30.83, 42.39, 61.40, 102.41, 131.84, 133.82, 138.99, 141.92.

Example 2

$^1$N,$^6$N,$^{11}$N,$^{16}$N,$^{21}$N,$^{26}$N,$^{31}$N,$^{36}$N-Octakis(mesitylensulfonyl)-1,6,11,16,21,26,31,36-octaazaoctatriacontane 4 was obtained starting with compound 3 (U.S. PAT APPL. 60/329, 982) following the homologation procedure described in WO 00/66587; namely, alkylation with 4-bromobutyronitrile, followed by reduction of the nitrile and protection of the free amino residue with mesitylenesulfonyl chloride. Starting with 7 g of 3, 5.6 g (70%) of 4 were obtained over the aforementioned three synthetic steps; $^1$HNMR (CDCl$_3$): 0.95 (t,3H), 1.30 (m, 28H), 2.30 (s, 24H), 2.55 (m, 48H), 2.75 (t, 1H), 3.0 (m, 30H), 6.95 (, 16H); $^{13}$CNMR (CDCl$_3$): 12.71, 20.93, 22.78, 24.49, 24.79, 25.68, 40.07, 41.91, 44.59, 44.95, 131.98, 133.39, 138.94, 139.96, 142.06.

Example 3

$^3$N,$^8$N,$^{13}$N,$^{18}$N,$^{23}$N,$^{28}$N,$^{33}$N,$^{38}$N-Octakis(mesitylenesulfonyl)-3,8,13,18,23,28,33,38-octaaza-42-bromo-botetracontane 5

To a solution of amide 4 (5.6 g, 2.8 mmol) and 1,4-dibromobutane(3.6 g, 16.8 mmol) in 45 ml of DMF kept at 5° C. was added 135 mg (3.36 mmol) of NaH (60% dispersion in mineral oil) with constant stirring. The mixture was kept at 22° C. for 18 h; the solvent was then evaporated to dryness, the residue dissolved in chloroform, washed twice with a saturated solution of ammonium chloride, the organic layer separated, dried (Na$_2$SO$_4$) and evaporated to dryness. The residue was crystallized from ethyl acetate-hexane; 5.3 g (88%) of 5 were obtained; mp 109° C.; $^1$HNMR (CDCl$_3$): 0.95 (t, 3H), 1.40 (m, 32H), 2.30 (s, 24H), 2.50 (m, 48H), 3.00 (m,32H), 3.25 (t, 2H), 6.95 (s, 16H); $^{13}$CNMR (CDCl$_3$): 12.68, 20.89, 22.68, 24.42, 25.78, 29.61, 32.77, 40.03, 44.51, 44.89, 45.04, 131.95, 133.46, 139.91, 142.28.

Example 4

$^3$N,$^8$N,$^{13}$N,$^{18}$N,$^{23}$N,$^{28}$N,$^{33}$N,$^{38}$N,$^{43}$N-Nonakis(mesitylenesulfonyl)-3,8,13,18,23,28,33,38,43-nonaaza-heptatetracontylaldehyde diethyl acetal 6

To a solution of amide 5 (5.19 g, 2.43 mmol) and acetal 2 (0.915 g, 2.67 mmol) in 50 ml of DMF kept at 5° C. was added 128 mg (3.20 mmol) of NaH (60% dispersion in mineral oil) with constant stirring. The mixture was kept at 22° C. for 18 h and the work up followed the procedure reported for $^5$; 5.0 g (86%) of 6 were obtained; mp 102.4° C.; $^1$HNMR (CDCl$_3$): 0.95 (t, 3H), 1.15 (t, 6H ), 1.30 (m, 36H), 2.30 (s, 27H), 2.50 (s, 54H), 3.05 (m,36H), 3.45 (m,m, 4H), 6.95 (s,18H); $^{13}$CNMR (CDCl$_3$): 12.68, 15.26, 20.89, 22.67, 24.57, 30.81, 40.04, 4456, 44.88, 45.23, 102.31, 131.88, 133.39, 139.91, 142.19.

Example 5

$^3$N,$^8$N,$^{13}$N,$^{18}$N,$^{23}$N,$^{28}$N,$^{33}$N,$^{38}$N,$^{43}$N-Nonakis(mesitylenesulfonyl)-3,8,13,18,28,33,38,43-nonaaza-heptatetracontylaldehyde 7

Acetal 6 (5.0 g) was dissolved in acetone (140 ml) and water (1.5 ml), Amberlyst-15 resin (600 mg) was added and the reaction mixture was stirred for 1 h; the resin was filtered, the solvent evaporated to dryness in vacuo, and the oily residue was used in the next step without further purification; $^1$HNMR (CDCl$_3$): 0.95 (t,3H), 1.30(m,36H), 1.72 (m,2H), 2.30 (s,27H), 2.52(s,s, 54H), 3.05 (m,36H), 6.95(s,18H), 9.60 (s, 1H); $^{13}$CNMR (CDCl$_3$): 12.85, 19.89, 21.07, 22.92, 24.60, 24.92, 40.21, 40.79, 44.73, 45.06, 132.13, 133.54, 140.10, 142.47, 200.94; MS (MALDI): 2345.2 (M+Na$^+$), 2361.2 (M+K$^+$).

Example 6

$^3$N,$^8$N,$^{13}$N,$^{18}$N,$^{23}$N,$^{28}$N,$^{33}$N,$^{38}$N,$^{42}$N-Nonakis(mesitylenesulfonyl)-3,8,13,18,23,28,33,38,42,47-decaaza-nonatetracontane 8

To a solution of 4.2 g (1.7 mmol ) of aldehyde 7 in 120 ml of DCE, were added 7 ml (8 eq) of a 2M solution of ethylamine in THF. The mixture was kept at 22° C. for 18 h with constant stirring, after which sodium triacetoxyborohydride (720 mg, 3.4 mol) was added. After 2 h at 22° C., the mixture was washed (2×20 ml) with a saturated solution of sodium bicarbonate, dried, and evaporated to dryness. The residue was purified by flash chromatography using Cl$_3$CH/MeOH (5% to 10%) as eluant; 2.8 g (68%) of 8 were recovered; $^1$HNMR (Cl$_3$CD): 0.95 (t,3H), 1.10 (t,3H), 1.30 (m, 36H), 2.25 (s, 27H), 2.50(m, 58H), 3.05 (m, 36H), 2.25 (s, 27H), 2.50 (m, 58H), 3.05 (m, 36H), 6.95 (s, 18H); $^{13}$CNMR (CDCl$_3$): 12.66, 14.53, 20.89, 22.74, 24.70, 39.99, 43.73, 44.50, 44.84, 45.17, 48.57, 131.93, 133.31, 139.90, 142.28; MS (MALDI): 2351.92 (M+H$^+$), 2373.10 (M+Na$^+$), 2389.97 (M+K$^+$).

Example 7

Mesoporphyrin IX-bis[$^3$N,$^8$N,$^{13}$N$^{18}$N,$^{23}$N,$^{28}$N,$^{33}$N,$^{38}$N,$^{42}$N-nonakis(mesitylenesulfonyl)-3,8,13,18,23,28,33,38,42,47-decaazanonatetracontyl amide] 9

A mixture of amine 8 (750 mg, 0.3 mmol), mesoporphyrin IX (102 mg, 1.4 mmol), and diisopropylethylamine (0.25 ml, 1.4 mmol) in 30 ml of DMF were cooled to 5° C. and kept under a nitrogen atmosphere while 204 mg (0.54 mmol) of HBTU were added. The reaction mixture was stirred for 2 h, the solvent evaporated to dryness, the residue dissolved in chloroform, washed twice with a saturated bicarbonate solution, the organic layer dried (Na$_2$SO$_4$) and evaporated to dryness. The residue was purified by chromathography on silica gel using ethyl acetate:hexane (9:1) as eluant; 630 mg (75%) of 9 were recovered; MS (ESI): 5239.3 (M+H$^+$); 5261.3 (M+Na$^+$).

Example 8

Porphyrin conjugate SL-11211 eicosahydrobromide

Porphyrin amide 9 (630 mg) was dissolved in a mixture of methylene chloride (12 ml). 30% hydrogen bromide in glacial acetic acid (12 ml), and phenol (900 mg). The reaction mixture was kept at 22° C. for 18 h with stirring, the reaction product was then extracted into water (35 ml), the aqueous layer washed with methylene chloride (3×12 ml), the aqueous solution evaporated to dryness, and the residue crystallized from water/ethanol; 300 mg of SL-11211 hydrobromide (86%) were obtained; mp. 250° C. (dec); MS (ESI): 1958.4 (M+H$^+$, free base), 1980 (M+Na$^+$).

Example 9

$^3$N,$^8$N,$^{13}$N-Tri(mesitylenesulfonyl)-3,8,13-triaza-17-bromoheptadecane 11

Intermediate 11 was prepared starting with 10 (ref) and following the procedure described for 5. Starting with 3.6 g of 10 were obtained 2.77 g (65%) of 11; $^1$HNMR (CDCl3): 0.98 (t,3H), 1.40 (m, 8H), 1.65 (m,4H), 2.30 (s, 9H), 2.60 (s,18H), 3.10 (m,12H), 3.30 (t, 2H), 6.95 (s,6H); $^{13}$CNMR (CDCl$_3$): 12.75, 20.91, 22.72, 24.58, 25.85, 29.66, 32.79, 40.07, 44.59, 45.10, 131.90, 133.23, 140.03, 142.32.

Example 10

$^3$N,$^8$N,$^{13}$N,$^{18}$N-Tetrakis(mesitylenesulfonyl)-3,8,13,18-tetraaza-doeicosanylaldehyde diethyl acetal 12

Prepared from 11 following the procedure described for 6. Starting with 2.8 g of 11 were obtained 3.5 g (97%) of acetal 12; $^1$HNMR (CDCl$_3$): 1.00 (t, 3H), 1.15 (t, 6H), 1.35 (m, 16H), 2.35 (s, 12H), 2.55(s, 24H), 2.10(m,16H), 3.50 (m, 4H), 4.35 (t,1H), 6.95(s, 8H); $^{13}$CNMR (CDCl$_3$): 12.70, 15.26, 20.87, 22.44, 24.52, 30.81, 40.04, 44.55, 45.00, 45.23, 61.18, 102.31, 131.87, 133.35, 139.97, 142.18.

Example 11

$^3$N,$^8$N,$^{13}$N,$^{18}$N-Tetrakis(mesitylenesulfonyl)-3,8,13,18-tetraaza-doeicosanylaldehyde 13

The aldehyde was obtained from 12 following the procedure described for 7. From 3.5 g of acetal 12, were obtained 2.9 g (90%) of aldehyde 13; $^1$HNMR (CDCl$_3$): 0.95 (t, 3H), 1.35(m, 12H), 1.75 (m,2H), 2.30(m, 14H), 2.45(s, 24H), 3.05 (m, 2H), 2.30 (m, 14H), 2.45 (s, 24H), 3.05 (m, 16H), 6.95 (s, 8H), 9.60 (s, 1H); $^{13}$CNMR (CDCl$_3$): 12.63, 19.68, 20.80, 22.67, 24.68, 26.32, 39.98, 40.54, 43.70, 44.50, 45.06, 131.88, 133.04, 140.32, 142.22, 200.71.

Example 12

$^3$N,$^8$N,$^{13}$N,$^{18}$N-Tetrakis(mesitylenesulfonyl)-3,8,13,18,23-pentaazapentacosane 14

Amine 14 was prepared from 13 following the procedure described for 8. Starting with 4.7 g of 13 were obtained 3.5 g (72%) of amine 14; $^1$HNMR (CDCl$_3$): 1.00 (t, 3H), 1.15(t, 3H), 1.40 (m, 16H), 2.30(s, 12H), 2.60 (m, 28H), 3.10(m, 16H), 6.95(s, 8H); $^{13}$CNMR(CDCl$_3$): 11.70, 12.65, 20.83, 22.69, 23.46, 24.67, 39.96, 42.59, 44.47, 45.07, 46.60, 131.81, 133.26, 139.82, 142.36.

Example 13

2,4-Disulfonyl-Deuteroporphyrin IX-bis[$^3$N,$^8$N,$^{13}$N,$^{18}$N-tetrakis(mesitylenesulfonyl)-3,8,13,18,23-pentaazapentacosyl amide] 15

Porphyrin conjugate 15 was prepared by condensation of 14 with deuteroporphyrin IX disulfonate following the procedure described for 9. From 200 mg of 14 and 70 mg of the porphyrin, 144 mg (55%) of 15 were obtained; MS(MALDI): 2808.79 (M+H$^+$), 2830.55 (M+Na$^+$), 2853 (M+2Na$^+$), 2875.52 (M+3Na$^+$).

Example 14

Porphyrin conjugate SL-11233 decahydrobromide

Conjugate SL-11233 was obtained from 15 following the procedure described for SL-11211. From 144 mg of 15 were obtained 60 mg (55%) of SL-11233 decahydrobromide; MS (ESI): 1350 (M+H$^+$, M=free base).

Example 15

2,4-Disulfonyl-Deuteroporphyrin IX-bis[$^3$N,$^8$N,$^{13}$N,$^{18}$N,$^{23}$N,$^{28}$N,$^{33}$N,$^{38}$N,$^{42}$N-nonakis(mesitylenesulfonyl)-3,8,13,18,23,28,33,38,42,47-decaaza-nonatetracontyl amide] 16

Porphyrin conjugate 16 was prepared by condensation of amine 8 (216 mg) and deuteroporphyrin IX disulfonate (34 mg) following the procedure described for 9; 140 mg (57%) of 16 were obtained; MS(MALDI): 5342 (M+H$^+$), 5363 (M+Na$^+$).

Example 16

Porphyrin conjugate SL-11235 eicosahydrobromide

Conjugate SL-11235 was obtained from 140 mg of 16 following the procedure described for the synthesis of SL-11211; 70 mg (72%) of SL-11235 eicosahydrobromide were obtained; MS (MALDI): 2062.0(M+H$^+$, M=free base), 1031 (M*/2), 688.0 (M*/3).

Example 17

N-Methyl mesoporphyrin IX-bis[$^3$N,$^8$N,$^{13}$N,$^{18}$N,$^{23}$N,$^{28}$N,$^{33}$N,$^{38}$N,$^{42}$N-nonakis(mesitylenesulfonyl)-3,8,13,18,23,28,33,38,42,47-decaaza-nonatetracontyl amide] 17

Amide 17 was prepared by condensation of amine 8 (404 mg) with N-methyl mesoporphyrin IX (50 mg) following the procedure described for 9; 226 mg (50%) of 17 were obtained; MS (MALDI): 5253 (M+H$^+$).

Example 18

Porphyrin conjugate SL-11236 eicosahydrobromide

SL-11236 was prepared from 215 mg of 17 following the procedure described for the synthesis of SL-11211; 75 mg (52%) of SL-11236 eicosahydrobromide were obtained; MS(MALDI): 1972.0 (M+H$^+$, M=free base), 1989.0 (M+NH$_4^+$), 986.6 (M*/2).

Example 19

Porphyrin conjugate SL-11237 decahydrochloride

SL-11237 was prepared by condensation of 424 mg (0.6 mmol) of amine 18 and 191 mg (0.3 mmol) of mesoporphyrin IX following the procedure described for 9. SL-11237 was purified by chromathography on silica gel using chloroform/methanol/ammonium hydroxide: 8/2/0.1 as eluant; the eluted residue was further crystallized from methanol/hydrogen chloride/ethyl acetate; 430 mg (73%) of SL-11237 decahydrochloride were obtained; MS(ESI): 1579.6 (M+H$^+$, M=free base), 1725.6 (M+4HCl), 1871.8 (M+8HCl), 790.23 (M$^+$/2), 527.21 (M$^+$/3), 790.23(M$^+$/2).

Synthesis of SL-11217

Example 20 trans-2-Cyanocyclopropanecarbonyl chloride 20

1N Sodium hydroxide (71.9 ml, 71.9 mmol) was added to a solution of nitrile 19 (Payne G B, *JOC* (1967) 32, 3351) (10.0 g, 71.9 mmol) in 40 ml of methanol. The mixture was stirred during 1h, the methanol was evaporated, conc. HCl was added to pH 2, the solution extracted with ethyl ether (3×30 ml), the pooled organic layers were dried (Na$_2$SO$_4$) and evaporated to dryness. The residual solid (7.4 g, 93%) was used in the next step without further purification. It was dissolved in thionyl chloride (13 ml), the mixture was heated to 65° C./4 h, the thionyl chloride was then distilled off and 20 was purified by distillation at 50° C./0.5 mm; 4.3 g (54% over two steps) were obtained; $^1$HNMR (Cl$_3$CD): 1.80 (m, 2H), 2.25 (m, 1H), 2.80 (m, 1H); $^{13}$CNMR (Cl$_3$CD); 8.62, 1701, 30.20, 117.46, 171.34.

Example 21 trans 2-Nitrile-1-(N-ethyl-N-mesitylenesulfonyl-aminobutyl)cyclopropanecarboxamide 21

A solution of acyl chloride 20 (4.36 g, 33.7 mmol) in THF (43 ml) was added dropwise to a solution of N-ethyl-N-(mesitylenesulfonyl)-1,4-diamine (10.0 g, 33.7 mmol) (ref) and triethylamine (2.9 ml) in 100 ml of THF while the mixture was kept at 5° C. under nitrogen. Triethylammonium chloride precipitated; the mixture is further kept at 22° C. during 18 h, then extracted with ethyl acetate (80 ml), the organic layer washed with 2N HCl (10 ml), then with a saturated ammonium chloride solution (10 ml), dried (Na$_2$SO$_4$), and evaporated to dryness. The residue was purified by flash chromathography on silica gel using hexane/ethyl acetate: 6/4 as eluant; 10.3 g (78%) of 21 were obtained; $^1$HNMR (CDCl$_3$): 10.2 (t, 3H), 1.35(m,1H), 1.55 (m, 5H), 1.90 (m, 1H), 2.05 (m, 1H), 2.35 (s, 3H), 2.60 (s, 6H), 3.25 (m, 6H), 6.35 (t, 1H), 6.95 (s, 2H); $^{13}$CNMR (Cl$_3$CD): 4.44, 12.59, 20.87, 22.62, 22.69, 25.00, 26.37, 39.42, 40.04, 44.63, 120.14, 131.91, 133.23, 140.00, 142.37, 168.17.

Example 22 trans 1N-(Mesitylenesulfonyl)-2N(mesitylenesulfonyl)-2N(1'-N,N-(mesitylenesulfonyl) ethylaminobutyl) 1,2-diaminomethylcyclopropane 22

Amide 21 (8.5 g, 21.7 mmol) was dissolved in 40 ml of THF, 156 ml of THF.1M BH3 were added and the solution was heated at 70° C. during 2 h. The solution was cooled to 5° C., 30 ml of 6N HCl was slowly added while stirring, and the mixture was kept at 5° C. during 18 h. The pH of the mixture was then adjusted to pH 10 with 50% potassium hydroxide, the oil that separated was extracted into chloroform (3×50 ml), the organic extracts were dried (Na$_2$SO$_4$), and evaporated to dryness. The residue was dissolved in 100 ml of chloroform, 50 ml of 2N sodium hydroxide were added, the mixture cooled to 5° C., and mesitylenesulfonyl chloride (8.2 g, 386 mmol) dissolved in 10 ml of chloroform were added with efficient stirring. After 2 h, the organic layer was separated, dried (Na$_2$SO$_4$), and evaporated to dryness. The residue was purified by flash chromathography on silica gel using hexane/ethyl acetate: 7/3 as eluant; 11.33 g (69% over two steps) of 22 were obtained; $^1$HNMR (Cl$_3$CD): 0.40 (t, 2H), 0.95 (m, 5H), 1.25 (m, 4H), 2.25 (s, 9H), 2.35–2.65 (m, s, s, 20H), 2.85–3.30 (m, 8H), 5.50 (t, 1H), 6.95 (s, 6H); $^{13}$CNMR (CDCl$_3$) 10.02, 12.63, 16.15, 17.57, 20.87, 22.63, 22,69, 22.89, 24.01, 24.61, 39.97, 44.49, 44.89, 46.52, 48.28, 131.85, 132.34, 133.39, 133.97, 139.01, 139.97, 140.30, 141.73, 142.22, 142.60; MS (TOF): 768.2 (M+Na$^+$), 784.2 (M+K$^+$).

Example 23

$^3$N,$^8$N,$^{13}$N-Tris(mesitylenesulfonyl)-17-iodo-((E)-10,11-cyclopropane)-3,8,13-triaza-heptadecane 23

Triamide 22 (10.3 g, 13.8 mmol) was dissolved in 100 ml of DMF, cooled to 5° C., and sodium hydride (662 mg, 16.5 mmol) was added. The reaction mixture reached 22° C. when 1,4-dibromobutane (29.8 g, 138 mmol) and sodium iodide (20.7 g, 138 mmol) were added, and the mixture was heated at 75° C. for 90 min. The solution was evaporated to dryness, the residue dissolved in chloroform, the solution was washed with sodium thiosulfate, dried (Na$_2$SO$_4$), and evaporated to dryness. The residue was purified on a silica gel column using hexane/ethyl acetate; from 8/2 to 7/3 as eluant; 10.8 g (84%) of 23 were obtained; $^1$HNMR (Cl$_3$CD): 0.40 (m, 2H), 0.80 (m, 2H), 1.02 (t, 3H), 1.40(m, 4H), 1.60 (m, 4H), 2.30 (s, 9H), 2.60 (s, 18H), 2.80–3.30 (m, 14H), 6.95 (s, 6H); $^{13}$CNMR (Cl$_3$CD): 5.73, 11.01, 12.73, 16.07, 20.93, 22.74, 24.41, 25.65, 27.96, 29.62, 30.35, 32.92, 40.03, 44.40, 44.58, 45,24, 131.93, 140.09, 142.34, 142.48.

Example 24

$^3$N,$^8$N,$^{13}$N,$^{18}$N-Tris(mesitylenesulfonyl)-((E)-10,11-cyclopropane) 3,8,13,18-tetraazaeicosane 24

Triamide 23 (10.8 g, 11.6 mmol) was dissolved in 25 ml of THF and a 2M ethylamine solution in methanol was added (150 ml). The solution was heated at 65° C. during 16 h, then evaporated to dryness, the residue dissolved in chloroform, the chloroform washed with a concentrated solution of ammonium chloride, dried (Na$_2$SO$_4$), evaporated to dryness, and the residue purified by column chromathography on silica gel using from 5% to 10% methanol in chloroform as an eluant; 9.3 g (94%) of 24 were obtained; $^1$HNMR (Cl$_3$CD): 0.40 (t, 2H), 0.80 (m, 3H), 1.03 (t, 3H), 1.20 (t, 3H), 1.35 (m, 4H), 1.55 (m,4H), 2.25 (s, 9H), 2.40–3.35 (s, m, 34H), 6.95 (s, 6H); $^{13}$CNMR (Cl$_3$CD): 11.02, 12.70, 13.70, 16.04, 20.90, 22.71, 24.37, 24.76, 25.57, 40.02, 43.43, 44.57, 45.18, 45.33, 48.02, 48.83, 131.91, 133.13, 140.04, 142.34; MS (ESI): 846 (M+H$^+$).

Example 25

Mesoporphyrin IX-bis[$^3$N,$^8$N,$^{13}$N,$^{18}$N-tris(mesitylenesulfonyl)-((E)-10,11-cyclopropane)-3,8,13,18-tetrazaeicosanylamide] 25

Porphyrin diamide 25 was prepared by the condensation of 8.9 g (10.5 mmol) of 24 and mesoporphyrin IX (3.2 g, 5 mmol) following the procedure described for 9; 9.24 g (83%) of 25 were obtained; MS (MALDI): 2241 (M+Na$^+$).

Example 26

SL-11217 octahydrobromide

SL-11217 was prepared by cleavage of the protecting groups of 4.6 g of 25 following the procedure described for the synthesis of SL-11211; 3.4 g (96%) of SL-11217 octahydrobromide were obtained; mp>250° C. (dec), crystallized from methanol/ethyl acetate; MS (ESI): 1128.2 (M+H+), 1150 (M+Na$^+$), 1167 (M+K$^+$), 564.6 (M$^+$/2).

Synthesis of SL-11209 dodecahydrochloride

Example 27

Benzyl $^3$N,$^8$N,$^{13}$N,$^{18}$N-Tetrakis(mesitylenesulfonyl)-3,8,13,18-tetraazauneicosanyl alcohol 27

A suspension of NaH (60% in mineral oil, 440 mg, 14 mmol) in DMF (50 ml) was slowly added to a stirred solution of benzyl-4-bromobutyl ether (3.33 g, 13.7 mmol) and amide 26 (5.41 g, 5.48 mmol) (WO 00/66587) in DMF (100 ml) kept at 5° C. The reaction mixture was stirred for 10 h at 50° C., quenched with 5 ml of H$_2$O at 0° C., and evaporated to dryness in vacuo. The residue was taken up in ethyl acetate, washed with H$_2$O, and purified on a silica gel column using ethyl acetate/hexane: 3/7 as eluant; 5.1 g, (81%) of 27 were obatained; $^1$H-NMR (CDCl$_3$): 0.97 (t, J=7.1 Hz, 3H), 1.2–1.5 (m, 16H), 2.27 (s, 3H), 2.29 (s, 9H), 2.55 (s, 24H), 2.9–3.2 (m, 16H), 3.31 (t, J=6.0 Hz), 4.41 (s, 2H), 6.9–7.0 (m, 8H), 7.2–7.4 (m, 5H).

Example 28

3,8,13,18-Tetrazauneicosanyl alcohol 28

A solution of 30% HBr in glacial acetic acid (90 ml) was added to a stirred solution of 27 (4.50 g) and phenol (12.65 g) in methylene chloride (45 ml) at 0° C. The cooling bath was removed and the reaction mixture was stirred for 24 h at 20° C. The reaction mixture was quenched with H$_2$O (90 ml), washed with methylene chloride, and concentrated to dryness in vacuo. The residue was cooled to 0° C., basified with 2N sodium hydroxide (9 ml), followed by 50% potassium hydroxide (9 ml). The product was extracted with chloroform (7×10 ml); 1.07 g (81%) of 28 were obtained; $^1$H-NMR (CDCl$_3$): 1.10 (t, J=7 Hz, 3H), 1.40–1.75 (m, 16H), 2.55–2.75 (m, 16H ), 3.57 (t, J=5.0 Hz); $^{13}$C-NMR (CDCl$_3$): 15.23, 27.55, 27.92, 28.58, 32.35, 44.02, 49.35, 49.66, 49.80, 62.32.

Example 29

$^3$N,$^8$N,$^{13}$N,$^{18}$N-Tetrakis(butyloxycarbonyl)-3,8,13,18-tetrazauneicosanyl alcohol 29

A solution of 10% sodium carbonate (26 ml) was added to a solution of tetramine 28 (634 mg, 1.92 mmol) in dioxane (16 ml). Di-tert-butyl dicarbonate (2.5 g, 11.5 mmol) in dioxane (16 ml) was added into the reaction mixture at 0° and stirred for 10 h at 20° C. The reaction mixture was diluted with chloroform (200 ml), washed with water, then with brine, dried (Na$_2$SO$_4$), evaporated to dryness, and purified by chromathography on a silica gel column using ethyl acetate/hexane: 4/6 as eluant; 1.34 g, (96%) of 29 were obtained; $^1$H-NMR (CDCl$_3$): 1.09 (t, J=7.1 Hz, 3H), 1.4–1.7 (m, 52 H), 3.05–3.3 (m, 16H), 3.67 (t, J=5.8 Hz, 2H).

Example 30

$^3$N,$^8$N,$^{13}$N,$^{18}$N-Tetrakis(butyloxycarbonyl)-3,8,13,18-tetrazauneicosanyl aldehyde 30

Oxalyl chloride (2N solution in methylene chloride, 0.821 µl, 1.64 mmol) was diluted with anhydrous methylene chloride (6 ml) at −60+ C. DMSO (223 µl, 2.59 mmol) in methylene chloride (3 ml) was added to the mixture, the latter stirred for 5 min at −60° C., and 29 (1.12 g, 1.53 mmol) dissolved in methylene chloride (9 ml) was added to the reaction mixture. After 30 min of stirring at −60° C., triethylamine (1.06 ml, 14.46 mmol) was added to the reaction mixture and the temperature was allowed to rise to 20° C. (ca. 1.5 h). The reaction mixture was diluted with methylene chloride, washed with H$_2$O, saturated sodium bicarbonate, and brine. The organic layer was concentrated to dryness in vacuo and purified by column chromatography on silica gel using ethyl/acetate/hexane: 3/7 as eluant; 989 mg (89%) of 30 were obtained; $^1$H-NMR (CDCl$_3$): 1.09 (t, J=7.0 Hz, 3H), 1.4–1.6 (m, 48H ), 1.84 (m, 2H ), 2.45 (t, J=6.8 2H), 3.05–3.3 (m, 16H), 9.78 (s, 1H).

Example 31

$^3$N,$^8$N,$^{13}$N,$^{18}$N,$^{23}$N-Tetrakis(butyloxycarbonyl)-3,8,13,18,23-pentaza-pentaeicosane 31

Platinum oxide (100 mg) was reduced in methanol (30 ml) with hydrogen at 30 psi. for 15 min. Aldehyde 30 (989 mg, 1.36 mmol) dissolved in a 2M solution of ethylamine in ethanol (7 ml) was added to the hydrogenation flask, and the mixture hydrogenated for 10 h at 50 psi. The catalyst was removed by filtration through celite and the filtrate was concentrated to dryness in vacuo; 1.0 g (99%) of 31 were obtained; $^1$H-NMR (CDCl$_3$): 1.09 (t, J=7.6 Hz, 3H), 1.12 (t, J=7.2 Hz, 3H), 1.3–1.65 (m, 50H, CH$_2$), 1.66 (m, 2H), 2.71 (m, 2H), 3.1–3.3 (m, 18H). MS-MALDI (m/z): 758.8 (M$^+$, 100%), 744 (30%).

Example 32

1 3,5,8-Tetramethyl-2,4-diethyl-6,7-di(propionaldehyde)porphyrin 32

Diisobutylaluminum hydride (1.16 ml of 1.5 M solution in toluene, 1.74 mmol) was added to a solution of mesoporphyrin IX dimethyl ester (500 mg, 0.84 mmol) in CH$_2$Cl$_2$ (10 ml) at −78° C., the mixture was stirred at this temperature for 1 h, then quenched with a saturated solution of NH$_4$Cl (1 ml), followed by a 3.7% solution of HCl (2 ml). The temperature of the reaction mixture was allowed to rise to 20° C., the product was extracted with CH$_2$Cl$_2$, dried (Na$_2$SO$_4$), and purified on a column of silica gel using ethyl acetate/hexane: 3/7 as eluant, 330 mg (73%) of 32 were obtained; $^1$HNMR (CDCl$_3$): 1.86 (t, J=7.6 Hz, 6H), 3.39 (t, J=7.4 Hz, 6H), 3.60 (s, 6H), 3.62 (s, 6H), 4.0–4.2 (m, 4H), 4.5–4.45 (m, 4H), 9.97 (s, 1H), 10.04 (s, 1H), 10.05 (s, 1H), 10.06 (s, 1H), 10.065 (s, 1H), 10.07 (s, 1H).

Example 33

SL-11209 dodecahydrochloride

Amine 31 (182 mg, 0.24 mmol) and dialdehyde 32 (58 mg, 0.11 mmol) were mixed in 1,2-dichloroetane (3 mL) and sodium triacetylborohydride (60 mg, 0.28 mmol) was added at 22° C., the mixture was stirred for 3.5 h and then quenched with a solution of sodium bicarbonate. The reaction mixture was diluted 3 times with chloroform, washed with H$_2$O, dried (Na$_2$SO$_4$) and concentrated to dryness in vacuo. The residue was dissolved in methylene chloride, cooled to 0° C. and trifluoroacetic acid added. After stirring for 1.5 h, the cooling bath was removed, the mixture was evaporated to dryness.

The residue was dissolved in 10% HCl, the aqueous layer washed with chloroform, and the water removed in vacuo; 134 mg (74%) of crude SL-11209 were obtained. The product was purified by HPLC (Column: 21.5 mm×250 mm, C$_{18}$ Dynamax, eluent A=0.1% TFA, eluent B=0.088% TFA in 90% acetonitrile). The pure product was dissolved in 10% HCl (5 mL), and evaporated to dryness in vacuo. $^1$H NMR (D$_2$O): 1.16 (t, J=7.0 Hz, 6H), 1.34 (t, J=7.3 Hz, 6H), 1.60–2.00 (m, 38H), 2.50–2.70 (m, 4H), 2.90–3.30 (m, 40 H) 3.50–3.65 (m, 4H), 3.75 (s, 6H), 3.82 (s, 6H), 4.20–4.35 (m, 4H), 4.45–4.60 (m, 4H), 10.5 (bs, 4H). MS (MALDI), 1240.6 [M+Na]$^+$, 1218.4, [M+1]$^+$.

SLIL-11210 dodecahydrochloride

Example 34

1,3,5,8-Tetramethyl-2,7-diethyl-6,7-bis[3'N,8'N,13'N, 18'N-tetrakis (mesitylenesulfonyl)-3',8',13',18',23'-pentaazaheptaeicosane]porphyrin 34

A solution of nitrile 33 (1.6 g, 1.5 mmol) (U.S. PAT APPL. 60/329,982) in ethanol (90 ml) and chloroform (1.6 ml) was hydrogenated in the presence of PtO$_2$ (160 mg) under 50 psi for 10 h, the suspension filtered through a celite cake, evaporated to dryness and dried in vacuo. The product was dissolved in 1,2-dichloroetane (10 mL), dialdehyde 32 (370 mg, 0.69 mmol) was added followed by triethylamine (0.23 ml, 1.67 mmol). The reaction was stirred for 20 h, after which sodium triacetylborohydride (352 mg, 1.66 mmol) was added and the mixture further stirred for 3.5 h. The reaction mixture was quenched with a solution of sodium bicarbonate, thrice its volume of chloroform was added; the organic layer was washed with H$_2$O, dried, and evaporated to dryness in vacuo. The residue was dissolved in methylene chloride (20 mL), cooled to 0° C., made basic with 2N sodium hydroxide (5 mL) and mesitylsulfonyl chloride (333 mg, 1.5 mmol) was added. After 10 h of stirring at 22° C. and following the usual workup the reaction product was purified by column chromatography on silica gel using chloroform/ethyl acetate; 9/1 as eluant; 729 mg (35%) of 34 were obtained; $^1$H NMR (CDCl$_3$): 0.93 (t, J=7.14 Hz), 1.05–1.50 (m,) 1.50–1.70 (m), 1.90 (t, J=7.14 Hz), 2.05 (s), 2.07 (s), 2.08 (s), 2.13 (s), 2.16 (s), 2.21 (s), 2.24 (s), 2.29 (s), 2.41 (s), 2.45 (s), 2.49 (s), 2.52 (s), 2.70–3.10 (m), 3.10–3.25 (m), 3.40–3.52 (m), 3.53 (s), 3.54 (s), 3.66 (s), 3.85–4.00 (m), 4.0–4.2 (m), 5.97 (s), 6.02 (s), 6.75 (s), 6.79 (s), 6.84 (s), 6.87 (s), 6.92 (s), 9.69 (s), 10.08 (s), 10.14 (s); MS (MALDI), 3007.02 [M+Na]$^+$, 2985.05 [M+1]$^+$, 2983.95 [M]$^+$, 1493.58 [M]$^{2+}$.

Example 35

SL-11210 dodecahydrochloride

SL-11210 was prepared from 34 following the procedure described for the synthesis of SL-11211. From 730 mg of 34 were obtained 360 mg (69%) of the dodecahydrobromide; $^1$HNMR (D$_2$O): δ 1.34 (t, J=7.3 Hz, 6H), 1.70–2.00 (m, 38H), 2.50–2.70 (m, 4H), 3.05–3.35 (m, 36H), 3.40–3.55 (m, 4H), 3.78 (2s, 6H), 3.82 (2s, 6H), 4.20–4.40 (m 4H), 4.40–4.60 (m, 4H), 10.40 (bs, 4H). MS (free base, MALDI), 1161.95 [M]$^+$. The dodecahydrobromide was converted into dodecahydrochloride after HPLC purification and treatment of the eluate with 20% HCl. MS (free base, MALDI), 1162.02 [M]$^+$, 581.82 [M]$^{2+}$.

Example 36

SL-11257 dodecahydrochloride

Amine 18 (310 mg, 0.44 mmol), dialdehyde 32(118 mg, 0.22 mmol), and triethylamine (0.16 ml) were dissolved in 27 ml of dichloroetane. The reaction was kept at 22° C. during 18 h, sodium triacetoxyborohydride (186 mg, 10.9 mmol) was then added, the reaction mixture was kept for further 2 h, it was then diluted with chloroform, the solution washed with saturated sodium bicarbonate, dried (Na$_2$SO$_4$), and evaporated to dryness. The residue was purified by column chromathography on silica gel using chloroform/methanol/ammonium hydroxide; 8/2/0.3 as eluant; 190 mg of SL-11257 were obtained. After purification by HPLC, 90 mg (20%) of pure material were obtained; MS (MALDI): 1551.8 (M+H$^+$, M=free base), 311.18 (M$^+$/2), 388.79(M$^+$/4), 517.8 (M$^+$/3), 776.03 (M$^+$/2).

Example 37

MTT Assay

A conventional MTT assay was used to evaluate percent cell survival. Exponentially growing monolayer cells were plated in 96-well plates at a density of 500 cells per well and allowed to grow for 24 hours. Serial dilutions of the drugs were added to the wells. Six days after drug treatment, 25 μl of MTT solution (5 mg/ml) was added to each well and incubated for 4 hours at 37° C. Then 100 μl of lysis buffer (20% sodium dodecyl sulfate, 50% DMF, and 0.8% acetic acid, pH 4.7) was added to each well and incubated for an additional 22 hours. A microplate reader ("EMAX"-brand, Molecular Devices, Sunnyvale, Calif.) set at 570 nm was used to determine the optical density of the cultures. Results are expressed as a ratio of the optical density in drug-treated wells to the optical density in wells treated with vehicle only. Tables 1, 2, and 3 below describe the results of the assays on various cell lines. FIGS. 1–13 also indicate the effects of the compounds on various cell lines.

Other suitable assays for testing the compounds of the invention are described in International Patent Application Nos. WO 00/66587 and WO 02/10142, and U.S. Pat. Nos. 6,392,098, 5,889,061, and 5,677,350

TABLE 1

Effect of Porphyrin Polyamine Analogues on Human Prostate Tumor Cell Growth by the MTT assay

| | $ID_{50}$ (μM) values for Human prostate tumor Cell Lines | | | | | |
|---|---|---|---|---|---|---|
| Compounds | DuPro | PC-3 | DU145 | LnCap | Tsu-pr1 | Tsu-pr1-ADR |
| SL-11209 | 1.4 | 1.7 | — | — | — | — |
| SL-11211 | 0.46 | 1.7 | — | — | 0.35 | 0.66 |
| SL-11217 | 3.6 | 2.8 | — | — | — | — |
| SL-11233 | 1.4 | 3.9 | >31.25 | >31.25 | — | — |
| SL-11235 | 0.12 | 0.45 | 0.17 | 0.2 | — | — |
| SL-11236 | 0.08 | 0.49 | 0.14 | 0.2 | — | — |
| SL-11237 | 1.9 | 1.7 | — | — | 1.87 | 12.62 |

— Not done

TABLE 2

Effect of Porphyrin Polyamine Analogs on Human Pancreatic Cancer Cell Growth by MTT Assay.

| | $ID_{50}$(μM) values for Human Pancreatic Cancer Cell Lines | |
|---|---|---|
| Compounds | BxPC-3 | Panc-1 |
| SL-11217 | 6.87 | 6.38 |
| SL-11237 | 5.92 | 12.45 |

TABLE 3

Effect of Porphyrin Polyamine Analogs on Human Brain Tumor Cell Growth by MTT Assay.

| Compounds | $ID_{50}$(μM) values for Human Brain Tumor Cells U251MG NCI |
|---|---|
| SL-11217 | 5.65 |
| SL-11237 | 2.30 |

Example 38

Oral Administration of SL-11237

Male athymic nude mice were given subcutaneous injections of $0.75 \times 10^6$ DU145 cells on Day 0. Beginning on Day 10, mice were treated once weekly for 3 weeks with acidified water, 100 mg/kg, or 500 mg/kg of SL-11237 via oral gavage at 10 ml/kg dosing volume (the third treatment was actually 400 mg/kg in the high dose group). The results are depicted in FIG. 14, where the top panel depicts average tumor volume in the mice. The bottom panel of FIG. 14 depicts average body weight of the mice. Oral administration thus provides an effective and convenient means of administering the compounds of the invention.

All references, publications, patents and patent applications mentioned herein are hereby incorporated by reference herein in their entirety.

Although the foregoing invention has been described in some detail by way of illustration and example for purposes of clarity and understanding, it will be apparent to those skilled in the art that certain changes and modifications may be practical. Therefore, the description and examples should not be construed as limiting the scope of the invention, which is delineated by the appended claims.

The invention claimed is:

1. A composition comprising a compound according to the formula

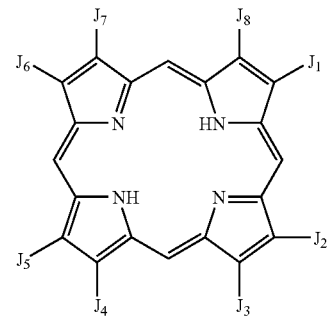

wherein at least one of $J_1$, $J_2$, $J_3$, $J_4$, $J_5$, $J_6$, $J_7$ and $J_8$ is independently M, where each M is independently selected from the group consisting of —(B-A-B)$_x$-G-(B-A-B)$_m$—(N(P)—B-A-B)$_n$—K wherein each A is independently selected from the group consisting of: a nonentity, $C_1$–$C_{12}$ alkyl, $C_2$–$C_{12}$ alkenyl, $C_2$–$C_{12}$ alkynyl, $C_3$–$C_{12}$ cycloalkyl, $C_3$–$C_8$ cycloaryl, $C_3$–$C_{12}$ cycloalkenyl, $C_3$–$C_{12}$ cycloalkynyl, $C_1$–$C_{12}$ alkanol, $C_3$–$C_{12}$ cycloalkanol, and $C_3$–$C_8$ hydroxyaryl;

each B is independently selected from the group consisting of: a nonentity, $C_1$–$C_{12}$ alkyl, $C_2$–$C_{12}$ alkenyl, $C_2$–$C_{12}$ alkynyl, $C_3$–$C_{12}$ cycloalkyl, $C_3$–$C_8$ cycloaryl, $C_3$–$C_{12}$ cycloalkenyl, $C_3$–$C_{12}$ cycloalkynyl, $C_1$–$C_{12}$ alkanol, $C_3$–$C_{12}$ cycloalkanol, and $C_3$–$C_8$ hydroxyaryl;

and with the proviso that each —B-A-B— unit contain at least one carbon atom;

wherein G is independently selected from the group consisting of —N(P)—, —(C=O)—N(P)—, —N(P)—(C=O)—, and a nonentity;

x is independently 0 or 1;

m is independently 0 or 1;

n is independently an integer from 0 to 20;

each P is independently selected from the group consisting of H and $C_1$–$C_{12}$ alkyl;

each K is independently selected from the group consisting of H, $C_1$–$C_{12}$ alkyl, $C_2$–$C_{12}$ alkenyl, $C_2$–$C_{12}$ alkynyl, $C_3$–$C_{12}$ cycloalkyl, $C_3$–$C_8$ cycloaryl, $C_3$–$C_{12}$ cycloalkenyl, $C_3$–$C_{12}$ cycloalkynyl, $C_1$–$C_{12}$ alkanol, $C_3$–$C_{12}$ cycloalkanol, and $C_3$–$C_8$ hydroxyaryl, and Q;

where each Q is independently selected from the group consisting of

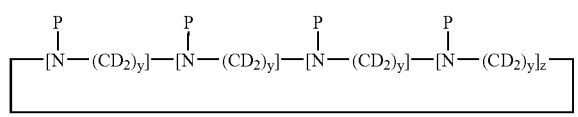

where each P is independently selected from the group consisting of H and $C_1$–$C_{12}$ alkyl, each D is selected from the group consisting of H and $C_1$–$C_{32}$ alkyl, y is an integer from 1 to 8, and z is an integer from 0 to 5, and where the Q moiety is attached to the remainder of the molecule at any C or N atom in the Q moiety (including C atoms in the D or P moieties) by removing a hydrogen atom, a P substituent, or a D substituent of the Q moiety to form an open valence for attachment to the remainder of the molecule;

and where the remaining members or member of $J_1$, $J_2$, $J_3$, $J_4$, $J_5$, $J_6$, $J_7$ and $J_8$ are each independently selected from the group consisting of H, —B-A-B, —COOH, —SO$_3$H, —B-A-B—COOH, or —B-A-B—SO$_3$H, where each A and each B are independently selected as defined above and with the proviso that each —B-A-B— unit has at least one carbon atom;

with the proviso that M excludes moieties of the form

—K$_1$-G$_5$-L$_5$-(N(P$_5$)-A$_5$)$_n$-K$_2$ where K$_1$ is independently selected from the group consisting of C$_1$–C$_8$ alkyl and where the valence to the left of K$_1$ attaches to the porphyrin ring;

G$_5$ is —O—, —(C=O)—, —C(=O)—O—, —O—(C=O)—, —O—(C=O)—O—, —O—(C=O)—N—, —N—(C=O)—O—, or a nonentity;

L$_5$ is C$_1$–C$_8$ alkyl, C$_3$–C$_8$ cycloalkyl, C$_3$–C$_8$ cycloaryl, C$_1$–C$_8$ alkoxy, C$_1$–C$_8$ alkyl-C$_3$–C$_8$ cycloalkyl, C$_1$–C$_8$ alkyl-C$_3$–C$_8$ cycloaryl, C$_1$–C$_8$ alkoxy-C$_3$–C$_8$ cycloaryl, C$_3$–C$_8$ cycloalkyl-C$_3$–C$_8$ cycloaryl, C$_3$–C$_8$ cycloalkyl-C$_1$–C$_8$ alkyl, C$_3$–C$_8$ cycloaryl-C$_1$–C$_8$ alkyl, C$_3$–C$_8$ cycloaryl-C$_1$–C$_8$ alkoxy, C$_3$–C$_8$ cycloaryl-C$_3$–C$_8$ cycloalkyl, or a nonentity;

each A$_5$ is independently selected from the group consisting of C$_1$–C$_8$ alkyl, C$_2$–C$_8$ alkenyl, C$_2$–C$_8$ alkynyl, C$_3$–C$_8$ cycloalkyl, C$_3$–C$_8$ cycloaryl, C$_3$–C$_8$ cycloalkenyl, and C$_3$–C$_8$ cycloalkynyl;

P$_5$ is selected from the group consisting of H and C$_1$–C$_8$ alkyl;

n is an integer from 2 to 8;

and K$_2$ is independently selected from the group consisting of H, C$_1$–C$_8$ alkyl, C$_2$–C$_8$ alkenyl, C$_2$–C$_8$ alkynyl, C$_3$–C$_8$ cycloalkyl, C$_3$–C$_8$ cycloaryl, C$_3$–C$_8$ cycloalkenyl, C$_3$–C$_8$ cycloalkynyl, C$_1$–C$_8$ alkanol, C$_3$–C$_8$ cycloalkanol, and C$_3$–C$_8$ hydroxyaryl;

wherein at least one K is Q, and where the Q moiety is attached to the remainder of the molecule at any N atom in the Q moiety by removing a P substituent of the Q moiety to form an open valence for attachment to the remainder of the molecule.

2. A composition comprising a compound according to the formula

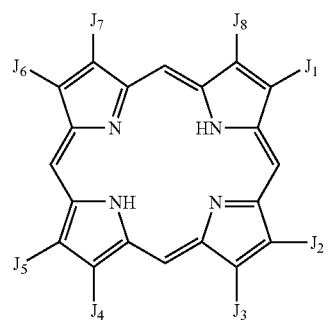

wherein at least one of $J_1$, $J_2$, $J_3$, $J_4$, $J_5$, $J_6$, $J_7$ and $J_8$ is independently M, where each M is independently selected from the group consisting of —(B-A-B)$_x$-G-(B-A-B)$_m$—(N(P)—B-A-B)$_n$—K wherein each A is independently selected from the group consisting of: a nonentity, C$_1$–C$_{12}$ alkyl, C$_2$–C$_{12}$ alkenyl, C$_2$–C$_{12}$ alkynyl, C$_3$–C$_{12}$ cycloalkyl, C$_3$–C$_8$ cycloaryl, C$_3$–C$_{12}$ cycloalkenyl, C$_3$–C$_{12}$ cycloalkynyl, C$_1$–C$_{12}$ alkanol, C$_3$–C$_{12}$ cycloalkanol, and C$_3$–C$_8$ hydroxyaryl;

each B is independently selected from the group consisting of: a nonentity, C$_1$–C$_{12}$ alkyl, C$_2$–C$_{12}$ alkenyl, C$_2$–C$_{12}$ alkynyl, C$_3$–C$_{12}$ cycloalkyl, C$_3$–C$_8$ cycloaryl, C$_3$–C$_{12}$ cycloalkenyl, C$_3$–C$_{12}$ cycloalkynyl, C$_1$–C$_{12}$ alkanol, C$_3$–C$_{12}$ cycloalkanol, and C$_3$–C$_8$ hydroxyaryl;

and with the proviso that each —B-A-B— unit contain at least one carbon atom;

wherein G is independently selected from the group consisting of —N(P)—, —(C=O)—N(P)—, —N(P)—(C=O)—, and a nonentity;

x is independently 0 or 1;

m is independently 0 or 1;

n is independently an integer from 0 to 20;

each P is independently selected from the group consisting of H and C$_1$–C$_{12}$ alkyl;

each K is independently selected from the group consisting of H, C$_1$–C$_{12}$ alkyl, C$_2$–C$_{12}$ alkenyl, C$_2$–C$_{12}$ alkynyl, C$_3$–C$_{12}$ cycloalkyl, C$_3$–C$_8$ cycloaryl, C$_3$–C$_{12}$ cycloalkenyl, C$_3$–C$_{12}$ cycloalkynyl, C$_1$–C$_{12}$ alkanol, C$_3$–C$_{12}$ cycloalkanol, and C$_3$–C$_8$ hydroxyaryl, and Q;

where each Q is independently selected from the group consisting of

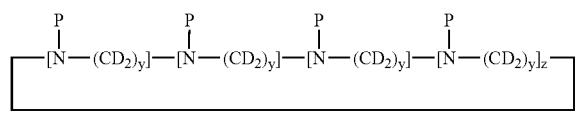

where each P is independently selected from the group consisting of H and C$_1$–C$_{12}$ alkyl, each D is selected from the group consisting of H and C$_1$–C$_{32}$ alkyl, y is an integer from 1 to 8, and z is an integer from 0 to 5, and where the Q moiety is attached to the remainder of the molecule at any C or N atom in the Q moiety (including C atoms in the D or P moieties) by removing a hydrogen atom, a P substituent, or a D substituent of the Q moiety to form an open valence for attachment to the remainder of the molecule;

and where the remaining members or member of $J_1$, $J_2$, $J_3$, $J_4$, $J_5$, $J_6$, $J_7$ and $J_8$ are each independently selected from the group consisting of H, —B-A-B, —COOH, —SO$_3$H, —B-A-B—COOH, or —B-A-B—SO$_3$H, where each A and each B are independently selected as defined above and with the proviso that each —B-A-B— unit has at least one carbon atom;

with the proviso that M excludes moieties of the form

—K$_1$-G$_5$-L$_5$-(N(P$_5$)-A$_5$)$_n$-K$_2$ where K$_1$ is independently selected from the group consisting of C$_1$–C$_8$ alkyl and where the valence to the left of K$_1$ attaches to the porphyrin ring;

G$_5$ is —O—, —(C=O)—, —C(=O)—O—, —O—(C=O)—, —O—(C=O)—O—, —O—(C=O)—N—, —N—(C=O)—O—, or a nonentity;

L$_5$ is C$_1$–C$_8$ alkyl, C$_3$–C$_8$ cycloalkyl, C$_3$–C$_8$ cycloaryl, C$_1$–C$_8$ alkoxy, C$_1$–C$_8$ alkyl-C$_3$–C$_8$ cycloalkyl, C$_1$–C$_8$ alkyl-C$_3$–C$_8$ cycloaryl, C$_1$–C$_8$ alkoxy-C$_3$–C$_8$ cycloaryl, C$_3$–C$_8$ cycloalkyl-C$_3$–C$_8$ cycloaryl, C$_3$–C$_8$ cycloalkyl- $C_1$–$C_8$ alkyl, $C_3$–$C_8$ cycloaryl-$C_1$–$C_8$ alkyl, $C_3$–$C_8$ cycloaryl-$C_1$–$C_8$ alkoxy, $C_3$–$C_8$ cycloaryl-$C_3$–$C_8$ cycloalkyl, or a nonentity;

each $A_5$ is independently selected from the group consisting of $C_1$–$C_8$ alkyl, $C_2$–$C_8$ alkenyl, $C_2$–$C_8$ alkynyl, $C_3$–$C_8$ cycloalkyl, $C_3$–$C_8$ cycloaryl, $C_3$–$C_8$ cycloalkenyl, and $C_3$–$C_8$ cycloalkynyl;

$P_5$ is selected from the group consisting of H and $C_1$–$C_8$ alkyl;

n is an integer from 2 to 8;

and $K_2$ is independently selected from the group consisting of H, $C_1$–$C_8$ alkyl, $C_2$–$C_8$ alkenyl, $C_2$–$C_8$ alkynyl, $C_3$–$C_8$ cycloalkyl, $C_3$–$C_8$ cycloaryl, $C_3$–$C_8$ cycloalkenyl, $C_3$–$C_8$ cycloalkynyl, $C_1$–$C_8$ alkanol, $C_3$–$C_8$ cycloalkanol, and $C_3$–$C_8$ hydroxyaryl;

wherein at least one A substituent comprises a cyclopronyl group.

3. A composition comprising a of to the formula

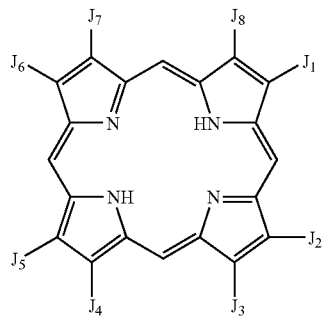

where $J_1$ and $J_2$ are independently M and each M is independently selected from the group consisting of —(B-A-B)-G-(B-A-B)-(N(P)—B-A-B)$_n$—K;

$J_3$, $J_4$, $J_6$ and $J_8$ are independently selected from methyl and ethyl; and $J_5$ and $J_7$ are independently selected from methyl, ethyl, and —SO$_3$H;

wherein at least one B-A-B comprises a cycloalkyl moiety.

4. The composition of claim 3, wherein at least one B-A-B unit comprises a cyclopropyl moiety.

5. The composition of claim 4, where $J_1$ and $J_2$ are identical.

6. A composition comprising a compound according to the formula

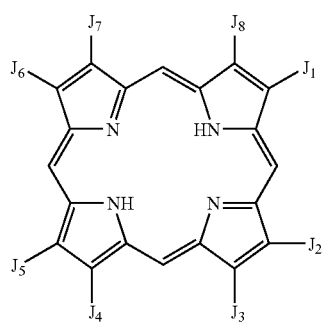

wherein at least one of $J_1$, $J_2$, $J_3$, $J_4$, $J_5$, $J_6$, $J_7$ and $J_8$ is independently selected from the group consisting of —(B-A-B)$_x$-G-(B-A-B)$_m$—(N(P)—B-A-B)$_n$—K wherein each A is independently selected from the group consisting of: a nonentity, $C_1$–$C_{12}$ alkyl, $C_2$–$C_{12}$ alkenyl, $C_2$–$C_{12}$ alkynyl, $C_3$–$C_{12}$ cycloalkyl, $C_3$–$C_8$ cycloaryl, $C_3$–$C_{12}$ cycloalkenyl, $C_3$–$C_{12}$ cycloalkynyl, $C_1$–$C_{12}$ alkanol, $C_3$–$C_{12}$ cycloalkanol, and $C_3$–$C_8$ hydroxyaryl;

each B is independently selected from the group consisting of: a nonentity, $C_1$–$C_{12}$ alkyl, $C_2$–$C_{12}$ alkenyl, $C_2$–$C_{12}$ alkynyl, $C_3$–$C_{12}$ cycloalkyl, $C_3$–$C_8$ cycloaryl, $C_3$–$C_{12}$ cycloalkenyl, $C_3$–$C_{12}$ cycloalkynyl, $C_1$–$C_{12}$ alkanol, $C_3$–$C_{12}$ cycloalkanol, and $C_3$–$C_8$ hydroxyaryl;

and with the proviso that each —B-A-B— unit contain at least one carbon atom;

wherein G is independently selected from the group consisting of —N(P)—, —(C=O)—N(P)—, —N(P)—(C=O)—, and a nonentity;

x is independently 0 or 1;

m is independently 0 or 1;

n is independently an integer from 0 to 20;

each P is independently selected from the group consisting of H and $C_1$–$C_{12}$ alkyl;

each K is independently selected from the group consisting of H, $C_1$–$C_{12}$ alkyl, $C_2$–$C_{12}$ alkenyl, $C_2$–$C_{12}$ alkynyl, $C_3$–$C_{12}$ cycloalkyl, $C_3$–$C_8$ cycloaryl, $C_3$–$C_{12}$ cycloalkenyl, $C_3$–$C_{12}$ cycloalkynyl, $C_1$–$C_{12}$ alkanol, $C_3$–$C_{12}$ cycloalkanol, and $C_3$–$C_8$ hydroxyaryl, and Q;

where each Q is independently selected from the group consisting of

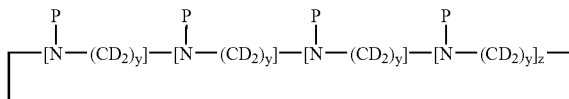

where each P is independently selected from the group consisting of H and $C_1$–$C_{12}$ alkyl, each D is selected from the group consisting of H and $C_1$–$C_{32}$ alkyl, y is an integer from 1 to 8, and z is an integer from 0 to 5, and where the Q moiety is attached to the remainder of the molecule at any C or N atom in the Q moiety (including C atoms in the D or P moieties) by removing a hydrogen atom, a P substituent, or a D substituent of the Q moiety to form an open valence for attachment to the remainder of the molecule;

and where the remaining members or member of $J_1$, $J_2$, $J_3$, $J_4$, $J_5$, $J_6$, $J_7$ and $J_8$ are each independently selected from the group consisting of H, —B-A-B, —COOH, —SO$_3$H, —B-A-B—COOH, or —B-A-B—SO$_3$H, where each A and each B are independently selected as defined above and with the proviso that each —B-A-B— unit has at least one carbon atom wherein each —K is independently Q;

where each Q is independently selected from the group consisting of

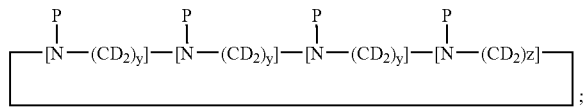

wherein only one D moiety is selected from the group consisting of $C_1$–$C_{32}$ alkyl and all remaining D moieties are H; wherein three P groups are selected from the group consisting of —H and —$CH_3$; wherein the fourth P group is absent and the Q moiety is attached to the remainder of the molecule at that valence; and wherein y is 2, 3, or 4 and z is 0, 1, or 2.

7. The composition of claim 1, wherein each —K is independently Q;

where each Q is independently selected from the group consisting of

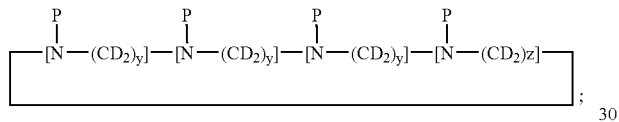

wherein only one D moiety is selected from the group consisting of $C_1$–$C_{32}$ alkyl and all remaining D moieties are H; wherein three P groups are selected from the group consisting of —H and —$CH_3$; wherein the fourth P group is absent and the Q moiety is attached to the remainder of the molecule at that valence; and wherein y is 2, 3, or 4 and z is 0, 1, or 2.

8. The composition of claim 1, wherein each —K is independently Q;

where each Q is independently selected from the group consisting of

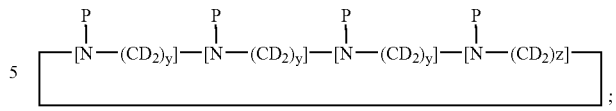

wherein only one D moiety is selected from the group consisting of $C_1$–$C_{32}$ alkyl and all remaining D moieties are H; wherein three P groups are selected from the group consisting of —H and —$CH_3$; wherein the fourth P group is absent and the Q moiety is attached to the remainder of the molecule at that valence; and wherein y is 2, 3, or 4 and z is 0, 1, or 2.

9. The composition of claim 6, wherein —K is

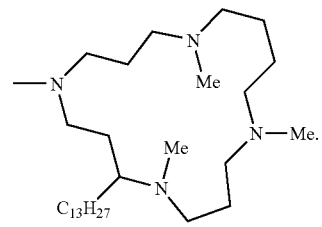

10. The composition of claim 1, wherein —K is

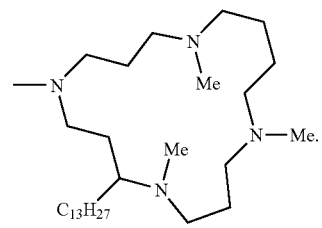

11. The composition of claim 1, further comprising a pharmaceutically acceptable carrier.

12. The composition of claim 2, further comprising a pharmaceutically acceptable carrier.

13. The composition according to claim 2, wherein the compound is

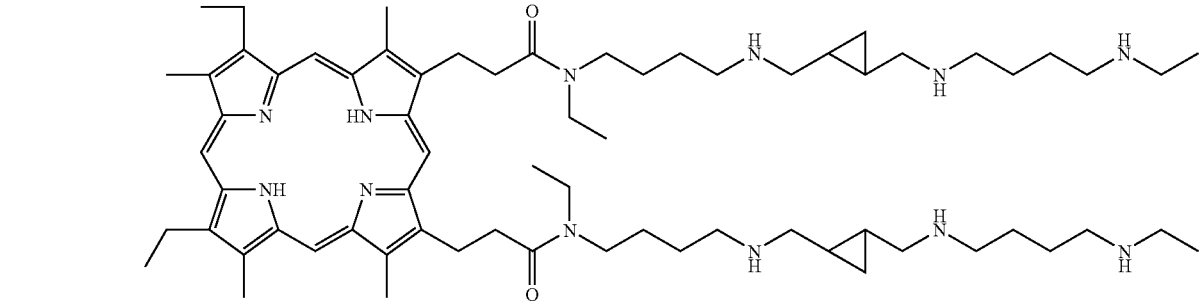

and all salts thereof.

14. The composition according to claim 10, wherein the compound is
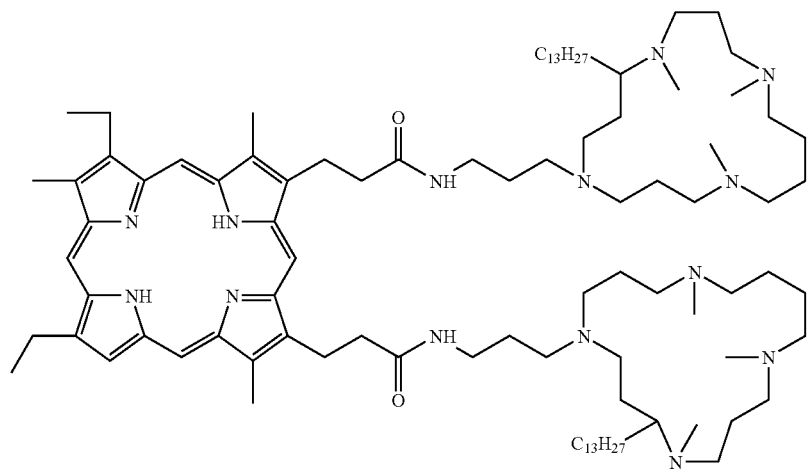
and all salts thereof.
15. The composition of claim 13, further comprising a pharmaceutically acceptable carrier.
16. The composition of claim 14, further comprising a pharmaceutically acceptable carrier.
* * * * *